United States Patent
Struys et al.

(10) Patent No.: US 9,757,045 B2
(45) Date of Patent: Sep. 12, 2017

(54) SYSTEM AND METHOD FOR ADAPTIVE DRUG DELIVERY

(75) Inventors: Michel M R F Struys, Belsele (BE); Tom De Smet, Temse (BE); Steven L. Shafer, Mountain View, CA (US)

(73) Assignee: Universiteit Gent, Gent (BE)

( * ) Notice: Subject to any disclaimer, the term of this patent is extended or adjusted under 35 U.S.C. 154(b) by 2448 days.

(21) Appl. No.: 11/044,445

(22) Filed: Jan. 27, 2005

(65) Prior Publication Data
US 2006/0167722 A1 Jul. 27, 2006

Related U.S. Application Data

(60) Provisional application No. 60/539,472, filed on Jan. 27, 2004.

(51) Int. Cl.
*G06Q 10/00* (2012.01)
*G06Q 50/00* (2012.01)
(Continued)

(52) U.S. Cl.
CPC ........ *A61B 5/02055* (2013.01); *A61B 5/4821* (2013.01); *A61B 5/4839* (2013.01);
(Continued)

(58) Field of Classification Search
CPC ................................................. A61B 5/02055
(Continued)

(56) References Cited

U.S. PATENT DOCUMENTS

| 4,403,984 A | 9/1983 | Ash et al. |
| 4,533,346 A * | 8/1985 | Cosgrove et al. ............ 604/66 |

(Continued)

FOREIGN PATENT DOCUMENTS

| EP | 1136090 | 9/2001 |
| EP | A-1 136 090 | 9/2001 |

(Continued)

OTHER PUBLICATIONS

De Smet et al., RUGLOOP as PK.TCI program (formerly at http://pkpd.icon.palo-alto.med.va.gov/).
(Continued)

*Primary Examiner* — Michelle L Le
(74) *Attorney, Agent, or Firm* — Haley Guiliano LLP

(57) ABSTRACT

The present invention provides a system and method for determining and maintaining a concentration level of medication in a patient sufficient to achieve and maintain a desired effect on that patient. Generally speaking, in accordance with one embodiment of the invention, a medication delivery controller uses a patient response profile to determine a concentration of medication in the patient that will achieve the desired effect on the patient. The patient response profile is a graphical, tabular or analytical expression of the relationship between the concentration of a medication and the effect of the medication at the specific concentration. Using this information, the medication delivery controller provides instructions to a medication delivery unit such as, for example, an infusion pump or inhalation device, to deliver the medication to the patient at a rate that will achieve the desired concentration level of the medication in the patient.

15 Claims, 9 Drawing Sheets

(51) Int. Cl.

| | | |
|---|---|---|
| *A61B 5/0205* | (2006.01) | |
| *A61B 5/00* | (2006.01) | |
| *G06Q 50/24* | (2012.01) | |
| *A61B 5/021* | (2006.01) | |
| *A61B 5/024* | (2006.01) | |
| *A61B 5/0402* | (2006.01) | |
| *A61B 5/0482* | (2006.01) | |

(52) U.S. Cl.
CPC .............. *G06Q 50/24* (2013.01); *A61B 5/021* (2013.01); *A61B 5/024* (2013.01); *A61B 5/0402* (2013.01); *A61B 5/0482* (2013.01)

(58) Field of Classification Search
USPC .......... 600/300, 500, 544; 705/2–4; 604/66, 604/500; 128/200
See application file for complete search history.

(56) References Cited

U.S. PATENT DOCUMENTS

| | | | |
|---|---|---|---|
| 4,705,503 A | | 11/1987 | Dorman et al. |
| 4,741,732 A | | 5/1988 | Crankshaw et al. |
| 5,109,850 A | | 5/1992 | Blanco et al. |
| 5,496,537 A | | 3/1996 | Henry et al. |
| 5,609,575 A | | 3/1997 | Larson et al. |
| 5,665,065 A | | 9/1997 | Colman et al. |
| 5,792,069 A | | 8/1998 | Greenwald et al. |
| 5,813,397 A | | 9/1998 | Goodman et al. |
| 5,860,957 A | | 1/1999 | Jacobsen et al. |
| 6,016,444 A | * | 1/2000 | John ..................... 600/544 |
| 6,042,579 A | | 3/2000 | Elsberry et al. |
| 6,053,887 A | | 4/2000 | Levitas et al. |
| 6,122,536 A | | 9/2000 | Sun et al. |
| 6,231,560 B1 | * | 5/2001 | Bui et al. ............... 604/500 |
| 6,261,280 B1 | | 7/2001 | Houben et al. |
| 6,599,281 B1 | | 7/2003 | Struys et al. |
| 6,605,072 B2 | | 8/2003 | Struys et al. |
| 6,622,036 B1 | * | 9/2003 | Suffin ..................... 600/544 |
| 2001/0022182 A1 | | 9/2001 | Heitmeier et al. |
| 2003/0045858 A1 | | 3/2003 | Struys et al. |

FOREIGN PATENT DOCUMENTS

| | | |
|---|---|---|
| WO | WO-93/14807 | 8/1993 |
| WO | WO-98/50095 | 11/1998 |
| WO | WO-00/67820 | 11/2000 |
| WO | WO-03/059422 | 7/2003 |
| WO | WO-03/080157 | 10/2003 |

OTHER PUBLICATIONS

De Smet, "Ontwerp van een Computergestuurd Closed-Loop Anesthesiesysteem," Thesis filed at Dept. of Electronics and Information Systems, Faculty of Applied Sciences, University of Gent, Academic Year 1994-1995.

Numerical Recipes in C: The Art of Scientific Computing, 2nd Edition, Cambridge Univ. Press, NY, NY, 1992, Chapter 15.5, pp. 681-688.

Shafer, Steven L., et al., "Algorithms to Rapidly Achieve and Maintain Stable Drug Concentrations at the Site of Drug Effect with a Computer-Controlled Infusion Pump," Journal Pharmacokinetics and Biopharmaceutics, 1992, vol. 20, No. 2, pp. 147-169.

Shafer, Steven L., et al., "Testing Computer-Controlled Infusion Pumps by Simulation," Anesthesiology, 1988, vol. 68, pp. 261-266.

Shafer, Steven L., STANPUMP User's Manual, Apr. 29, 1998, Stanpump—PK TCI Program, pp. 1-24.

Sheiner et al., "Simultaneous Modeling of Pharmacokinetics and Pharmacodynamics: Application to d-tubocurarine," Clin. Pharmacol. Ther., vol. 25(3): 358-371 (Mar. 1979).

Billard et al., "A comparison of spectral edge, delta power, and bispectral index as EEG measures of alfentanil, propofol, and midazolam drug effect," Clin. Pharmacol. Ther., vol. 61(1): 45-68 (Jan. 1997).

De Smet, "Ontwerp van een Computergestuurd Closed-Loop Anesthesiesysteem," Thesis filed at Dept. of Electronics and Information Systems, Faculty of Applied Sciences, University of Gent., (1995).

European search report issued for Application No. 05712018, issued Jun. 18, 2009.

\* cited by examiner

SYSTEM AND METHOD FOR ADAPTIVE DRUG DELIVERY

CROSS-REFERENCE TO RELATED APPLICATION

This application claims priority under 35 U.S.C. §119(e) to U.S. provisional patent application No. 60/539,472 filed Jan. 27, 2004, entitled *System and Method for Adaptive Drug Delivery*, which is incorporated herein by reference in its entirety.

BACKGROUND OF THE INVENTION

Field of the Invention

The present invention relates generally to the administration of medication, and more particularly to a closed loop system and method for adaptively controlling the administration of medication.

Related Art

Intravenous drug administration is a well-known and commonly used technique for administering medication to a patient. Intravenous administration of a medication results in a blood concentration of the medication in a patient with the object of obtaining a desired effect on that patient. An appreciation of the interrelationship between drug dose, concentration, effect and time is fundamental in pharmacology. Such an appreciation can be gained by understanding a pharmacokinetic-pharmacodynamic (PK-PD) model. This model characterizes concentration, effect and dosage by analyzing the pharmacokinetic impact of the drug dose and then the pharmacodynamic effect the drug dose has on the patient.

Specifically, pharmacokinetics (PK) seeks to describe, understand and predict the time-course of drug concentration (usually in the blood); it quantifies the relationship between dose and concentration. Pharmacodynamics (PD) seeks to describe the time-course and magnitude of the physiological effect of that concentration; it quantifies the relationship between concentration and effect. Hence, the marriage of kinetics and dynamics provides insight into the time-course of drug effect, and forms a basis for optimizing and controlling drug dosage.

One concern associated with controlling the dose/effect relationship of medication arises from the accuracy of the drug effect measurement. Another concern arises from the fact that other factors can come into play, altering the dose-effect relationship for a patient. These concerns apply to medication in general and particularly to anesthetic drugs.

Because different anesthetic drugs have different effects and side effects, drug effect can be measured in different ways. At present there are a variety of clinical indicators used as the basis for the administration of drugs to achieve a specific anesthetic state. According to conventional wisdom, the depth of anesthesia and anesthetic drug effect is clinically judged by the observation of somatic (patient movement) and autonomic (increased heart rate and blood pressure, tearing and pupil dilation) reflexes. There are, however, case reports of awareness during surgery in unparalyzed patients in whom somatic reflexes were absent. Even though these cases are relatively rare, the occurrences indicate that the observation of spontaneous movement during surgery is not foolproof.

If muscle relaxants are also present in the patient in doses that prevent movement, adequacy of anesthesia is most often assessed by the observation of autonomic reflexes, although a relationship to awareness has not been established. Another confounding factor is that anesthetic effect may be modified by disease, drugs and surgical techniques. Further, the degree of interpatient variability in the dose/effect relationship of anesthetic agents is high. In actual clinical practice, opiates and other drugs may be used in conjunction with sedative anesthetics making the clinical evaluation of anesthetic depth even more difficult.

Another conventional measure of anesthetic depth and anesthetic drug effect is the electroencephalogram (EEG). However, because changes in EEG morphology are profound and also different for each type of anesthetic being administered, interpretation of subtle changes in the raw (unprocessed) EEG requires a trained electroencephalographer and thus is typically not done during anesthesia and sedation. For this reason, computer processing of the EEG is often employed to compress the large amount of information present in the raw EEG, while preserving the information relevant to the monitoring application.

Several EEG monitors have been designed for use in the operating room, intensive care unit and other settings. These devices perform data compression and produce trends of frequency content, amplitude, and asymmetry between channels. Two main approaches have been used for this purpose: Fourier analysis and bispectral analysis.

The Fourier analysis approach represents a complex waveform as a summation of sine waves of different frequencies and amplitudes. The power spectrum can be computed from a Fast Fourier Transform (FFT) analysis. The power spectrum is in turn used to calculate a number of descriptive measures such as the spectral edge frequency (frequency below which 95% of the power spectrum (SEF 95%) or 50% of the power (median frequency or MF) exists). These measures of the EEG are often used in anesthetic pharmacological research. However, the use of power spectrum EEG analysis during clinical anesthesia has been limited for several reasons. First, different drugs have different effects on these power spectral measures. Also, at low concentrations these drugs induce activation, but at higher concentrations the drugs cause EEG slowing, even introducing iso-electric EEG episodes, referred to as burst suppression. Thus, both low and high concentrations can cause a non-monotonic relationship between the power spectral measures and the patient's clinical state.

Bispectral analysis is a quantitative EEG analysis technique that has been developed for use during anesthesia. Bispectral analysis of EEG measures consistency of phase and power relationships among the various frequencies of the EEG. The Bispectral Index® (BIS®) developed by Aspect Medical Systems, Inc., Newton, Mass., which is derived from bispectral analysis of the EEG, is a single composite EEG measure that tracks EEG changes associated with the different anesthetic states.

Principles of pharmacokinetics have recently been used to develop various schemes of computerized infusion for intravenous anesthetics and sedative drugs. A computer is provided with mean population pharmacokinetic data for the drug to be used, including the desired plasma concentration. The computer then calculates the quantity of drug and the rate of infusion for a desired ("target") concentration; an infusion pump then delivers the required infusion rate and volume to achieve that target concentration. Such systems are referred to as Target Controlled Infusion (TCI) systems.

The problems of drug administration are not limited to anesthetic drugs, nor are they limited to intravenous delivery of medication. In clinical practice, there is no ideal plasma-concentration to produce a certain drug effect. The specific concentration required depends on factors such as individual pharmacological variability, the interaction with other simultaneously used drugs and the intensity of the surgical stimulus. In addition, since TCI is a model-based forward control only, the actual concentration realized by applying TCI techniques may vary widely due to inter-patient variability, clinical circumstances, and population characteristics.

A model-based adaptive drug delivery system and method is described by two of the inventors of the present invention in U.S. Pat. No. 6,605,072. This system estimates an individualized patient response profile using measured data points from the induction phase: the induction phase is executed in a controlled open-loop regimen, and the drug concentration versus effect for this specific patient is measured. From these measurements the patient-individualized relationship is determined and applied during closed-loop control to achieve better control. Deviations of the effect obtained from a specific administered pharmacological dose are used to shift the induction-phase response profile to match the currently observed conditions and to calculate the required change in drug administration rate.

This technique has several disadvantages:
  the induction phase in a typical surgery is limited in time. In addition, it is not possible during the induction phase to step through the entire range of anesthetic agent concentrations that may occur under surgery. Instead, mathematical characteristics of the assumed relationship (e.g., symmetry around $c_0$) are used to extrapolate the patient response profile for higher concentrations.
  measurement errors during induction may jeopardize accuracy of the patient response profile—no estimate is made on how closely the real data matches the estimated response profile.
  it is not possible to have the controller take over an already anesthetized patient of whom the current anesthetic state is unknown, due to the lack of induction-phase data.
  it is not possible to accommodate changes in the shape of the patient's response profile during surgery, thus correcting for the effects of saturation, stimulation, etc.; the induction phase curve is shifted, but retains its shape.

The current invention presents a method which overcomes these disadvantages.

SUMMARY OF THE INVENTION

The present invention provides a system and method for determining and maintaining a concentration level of medication in a patient sufficient to achieve and maintain a desired effect on that patient. Generally speaking, in accordance with one embodiment of the invention, a medication delivery controller uses a patient response profile to determine a concentration of medication in the patient that will achieve the desired effect on the patient. The patient response profile is a graphical, tabular or analytical expression of the relationship between the concentration of a medication and the effect of the medication at the specific concentration. Using this information, the medication delivery controller provides instructions to a medication delivery unit such as, for example, an infusion pump or inhalation device, to deliver the medication to the patient at a rate that will achieve the desired concentration level of the medication in the patient.

The invention initially establishes an individualized patient response profile by using a stepped or continuously increasing administration of medication from an unmedicated baseline condition to establish the patient's response to a range of medication concentrations. In the absence of such initial baseline data, the invention uses a population-based patient response profile. A measure of the effect of the medication on the patient is continuously acquired by the system, and stored along with the current concentration. This data is used by the medication delivery controller in conjunction with past data to continuously recalculate the patient response profile. If the patient's response profile has changed, the medication delivery controller calculates a new patient response profile which more appropriately approximates the patient's actual instantaneous response. The medication delivery controller uses this new patient response profile to determine a new concentration level of medication which is predicted to achieve the desired effect on the patient. Effect data is then collected to reflect the patient's response to this new concentration, and the recalculation of the response profile is repeated. The effect and drug concentration data collected during operation is thus used to continuously individualize the population-based patient response profile to reflect the specific patient's varying individual response during closed-loop control. If the patient's response has not changed, the new response profile will be identical to the previous profile.

In one example application of the invention, the medication delivery controller can be implemented to determine a desired concentration level of an anesthetic medication to provide a desired level of sedation for a patient. However, the invention can be implemented with any of a variety of different medications to determine and maintain a concentration level of medication that will result in the desired effect on the patient. The actually realized concentration may or may not be measured. Any offset in realized concentration is irrelevant though, since the system will detect that the measured effect still differs from the desired effect, and will adjust the desired concentration level accordingly.

In one embodiment, a sensor package having one or more sensors can be included to sense one or more attributes of the patient. These attributes can include one or more conditions of the patient, which are used in determining the effect of the medication on the patient. The sensor package provides measures quantifying these attributes to the medication delivery controller. For example, in the case of anesthetic drugs, attributes useful in determining the level of sedation of the patient can include the patient's electroencephalogram (EEG), as well as other attributes such as the patient's heart rate, blood pressure, and oxygen saturation. Measures quantifying these attributes such as, for example, the Bispectral Index of the patient's EEG can be determined and provided to the medication delivery controller. The medication delivery controller utilizes these measures to determine the level of sedation of the patient. Likewise, other attributes and their associated measures can be used to measure or otherwise quantify the effect of other types of medications on a patient.

The medication delivery controller utilizes one or more measures sampled from the sensor package to determine the effect of the medication on the patient. Based on the patient response profiles determined for the patient, the medication delivery controller instructs a medication delivery unit to deliver the medication to the patient at the desired rate or level to achieve the determined concentration.

The degree to which any of the parameters describing the response profile are allowed to be varied by the optimization algorithm may be controlled, so as to utilize prior knowledge or the expert opinion of a medical professional to improve the individualization of the response profile. In addition, since the relevance of the acquired effect measurements decreases with increased sample age, the invention weights the data inversely with sample age, assigning the greatest influence to the most recent effect data and potentially excluding data older than a certain age from use.

An advantage of the invention is that changes in a patient's response to a medication can be determined using information obtained from the sensor package. With this information, delivery parameters of the medication such as, for example, the infusion rate, can be adjusted to ensure that the desired effect on the patient is achieved and maintained. As a result of this adaptive feedback process, a desired effect of a medication on a patient can be automatically maintained even if the patient's response to the medication changes as a result of external stimuli.

Further features and advantages of the invention as well as the structure and operation of various embodiments of the invention are described in detail below with reference to the accompanying drawings.

BRIEF DESCRIPTION OF THE DRAWINGS

The present invention will be described with reference to the accompanying drawings. In the drawings, like reference numbers indicate identical or functionally similar elements. Additionally, the left-most digit(s) of a reference number identifies the drawing in which the reference number first appears.

DETAILED DESCRIPTION OF THE INVENTION

Overview of the Invention

The present invention is directed toward a system and method for controlling the delivery of medication to a patient using an adaptive feedback control system. According to one embodiment of the invention, a response profile is used to characterize the relationship between the patient's estimated medication concentration and the physiological effect of that medication concentration.

The response profile is used to provide the patient with a level of that medication to achieve the desired effect. The physiological response of the patient is monitored to determine whether the desired effect is maintained. The initial response profile may be one determined from varying medication concentrations administered during induction or from data collected from an earlier use of the invention of the same patient with the same medications. In the absence of patient-specific response profile data, a population-derived response profile may be used. Data characterizing both the medication concentration and the effect of that concentration on the patient are used to continuously recalculate the parameters of the response profile to adapt to changes in the patient's response resulting from acclimation, surgical manipulation or stimulation, the passage of time, effects of other medications or changing physiological conditions, or other occurrences which may alter the effect a medication has on the patient.

Example Environment

The invention can be implemented in any medication delivery environment where it is desired or required to achieve a predetermined effect, even where external stimuli may affect the dose/effect relationship. One such example environment is the intravenous infusion of anesthetic medication to a patient to achieve a desired depth of anesthesia. The invention is from time to time described herein in terms of this example environment. Description in these terms is provided for ease of discussion only. After reading this description, it will become apparent to one of ordinary skill in the art that the present invention can be implemented in any of a number of different medication delivery environments where it is desirable to monitor or adjust the delivery of medication to achieve a desired result.

Controlled Feedback Drug Delivery

Figure 1:
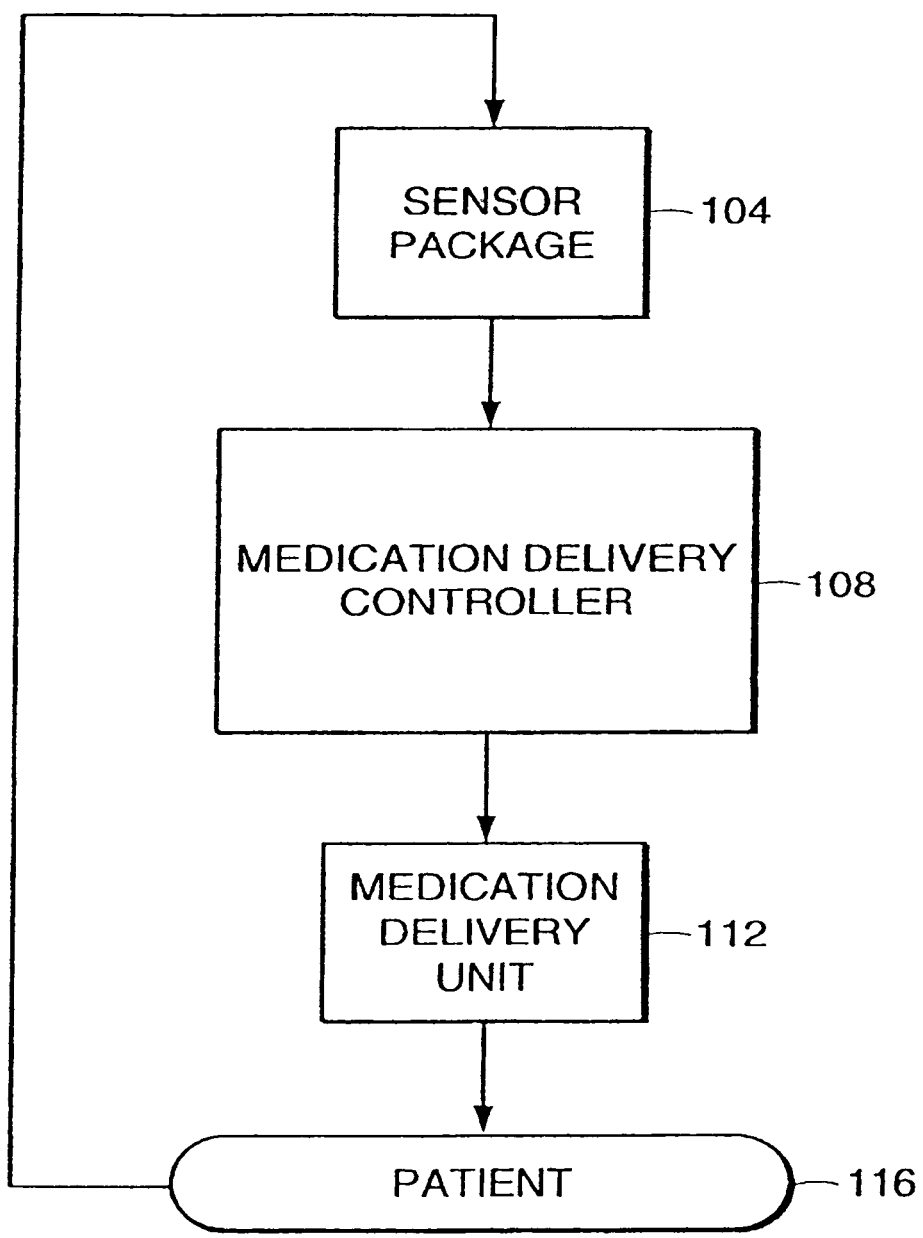
FIG. 1 is a block diagram illustrating a sensor package, medication delivery controller, and medication delivery unit in accordance with one embodiment of the invention.

FIG. 1 is a block diagram generally illustrating an application of a medication delivery controller in accordance with one embodiment of the invention. A patient 116 under surgical care, intensive care or other related healthcare is monitored by a sensor package 104 to determine the patient's response to a delivered medication. Sensor package 104 can include one or more sensors to sense the condition of or attributes of the patient. Sensor package 104 can provide measures such as, for example, patient blood pressure, heart rate, temperature, EEG measures, EKG measures or other measures representing the patient's overall condition or representing specific attributes about the patient.

Medication delivery controller 108 accepts the one or more measures and utilizes these measures to determine the desired concentration level of a medication. Medication delivery controller 108 controls medication delivery unit 112 to administer medication to patient 116 at the desired rate or interval to try to achieve the desired concentration of medication in the patient's blood stream. Medication delivery controller 108 controls medication delivery unit 112 such that the concentration of medication in the patient's blood stream is maintained, increased, or decreased. Decisions to maintain or adjust the rate or interval of medication delivery are made based on an evaluation of the measures received from sensor package 104.

Medication delivery unit 112 receives instructions from medication delivery controller 108 to adjust the rate or interval at which medication is delivered. Medication delivery unit 112 can be implemented as an infusion pump, inhalation device, or other medication delivery device. For example, in the case of an infusion pump, the medication delivery controller can adjust the infusion rate of medication delivery unit 112 to achieve a higher or lower blood level concentration of the subject medication in patient 116.

Figure 2:
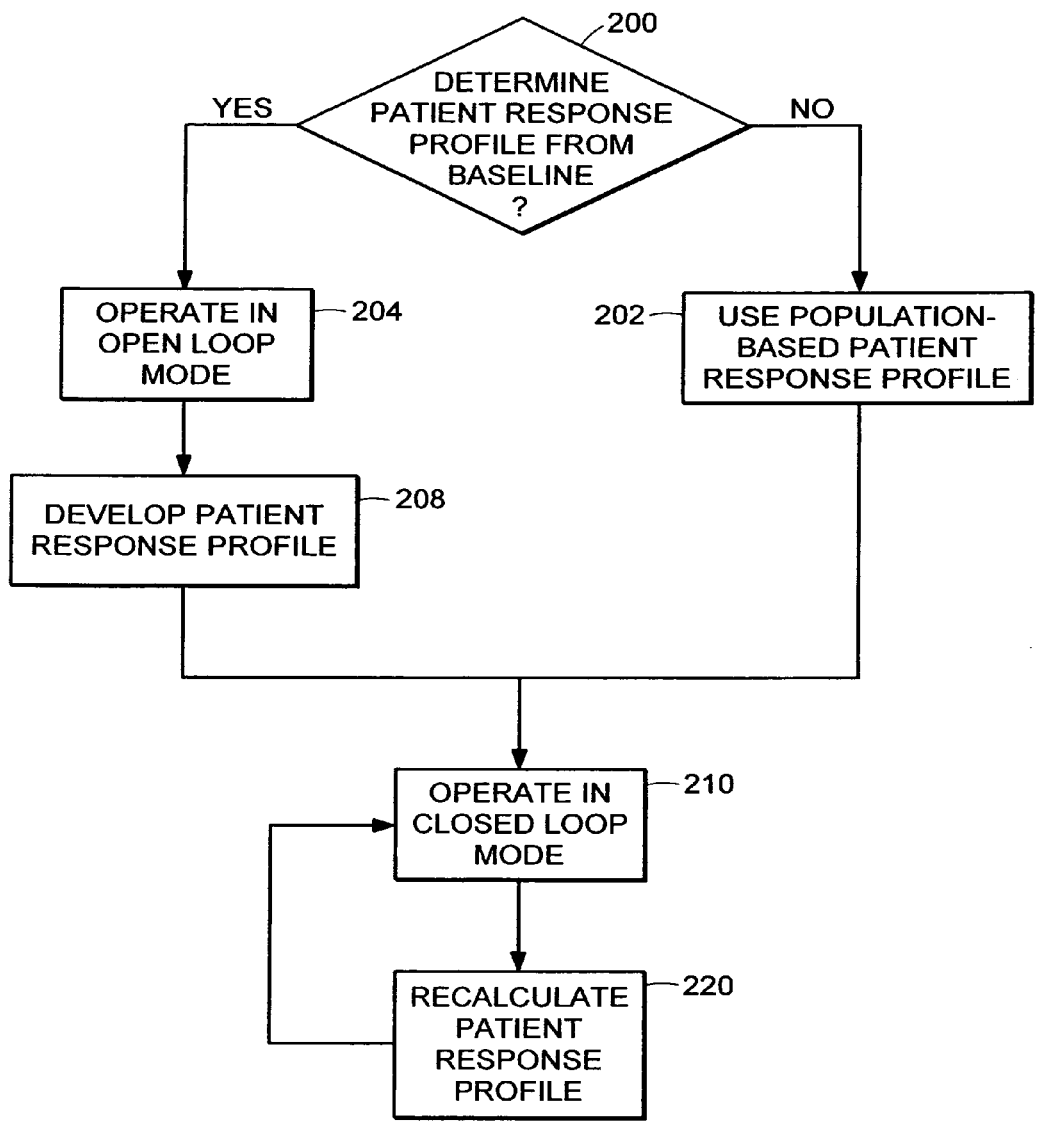
FIG. 2 is an operational flow diagram illustrating the process of developing an initial patient response profile either from an unmedicated baseline condition of from a population-based response profile in accordance with one embodiment of the invention.

FIG. 2 is an operational flow diagram illustrating the operation of medication delivery controller 108 according to one embodiment of the invention. In a decision step 200, a decision is made by the clinician operating the system whether to determine a patient response profile from an open loop delivery of medication or to use a population-derived patient response profile which is stored in the medication controller. While it is preferable to use the open loop mode option to determine an individual response profile, there are many situations in which this is not possible. For example, there may not be sufficient time to use the open loop option, or the patient may not be at an unmedicated baseline condition, so that the current medication concentration is unknown. In these situations, it is appropriate for the clinician operating the system to choose the population-based response profile. In a step 204, medication delivery controller 108 operates in an open loop mode, preferably without reference to the measures from sensor package 104 (except for safety). In this open-loop mode, medication delivery controller 108 controls medication delivery unit 112, such that varying concentrations of medication are delivered to patient 116 and the measures of the effect of such concentrations are received from sensor package 104.

In a step 208, a patient response curve, or response profile, is developed as a result of the open-loop operation. More particularly, measures received from sensor package 104 are used to track the effect of the medication on patient 116 at varying concentration levels and to derive an initial patient response profile. In a step 202, a population-based patient response profile is used for the starting condition.

Once the patient response profile is determined, medication delivery controller 108 operates in the closed-loop mode as illustrated by step 210. In the closed-loop mode, medication delivery controller 108 receives one or more measures from sensor package 104 reflecting the measured effect of the administered medication on patient 116. The available patient response profile is then applied in calculating the required change in drug administration rate. Because of external stimuli such as, for example, additional medication, surgical or invasive procedures, changing patient condition, or other factors affecting patient 116, the patient response profile may be altered. That is, the external stimuli may cause a patient to respond differently to a given concentration of medication. As such, in a closed-loop mode, medication delivery controller 108 in a step 220 uses the measures received from the sensor package 104 as well as the administered concentration and parameters describing the current patient response profile to calculate an updated set of parameters for the patient response profile used in step 210. This updated response profile will enable a better update of the drug administration rate. The parameters completely describe the response profile and thus updating the parameters is equivalent to updating the response profile, adapting the current calculated response profile to changes in the patient's response profile. If the patient response profile has changed, the updated parameters will change as well and in a step 210, the medication delivery controller 108 continues to operate in the closed-loop mode, using the updated patient response profile to calculate a new medication administration rate predicted to maintain the desired effect. If, for example, a higher concentration of medication is required to achieve or maintain a desired effect on the patient, medication delivery controller 108 instructs medication delivery unit 112 to adjust the rate at which the medication is administered to the patient. For example, where medication delivery unit 112 is an infusion pump, medication delivery controller 108 may instruct medication delivery unit 112 to increase the infusion rate, thereby increasing the concentration of medication in the patient's blood stream.

As stated above, before operating in the closed loop mode it is preferable that a patient response profile is determined from an unmedicated baseline since the effect of the medication on the patient is often highly individualized. However, in actual practice this determination is often not feasible. To facilitate use in these situations, the medication delivery controller 108 is therefore preprogrammed with pre-determined response profiles could be provided developed from normative populations. These predetermined profiles may be adjusted based on patient attributes such as height, weight, gender, etc.

Figure 3:
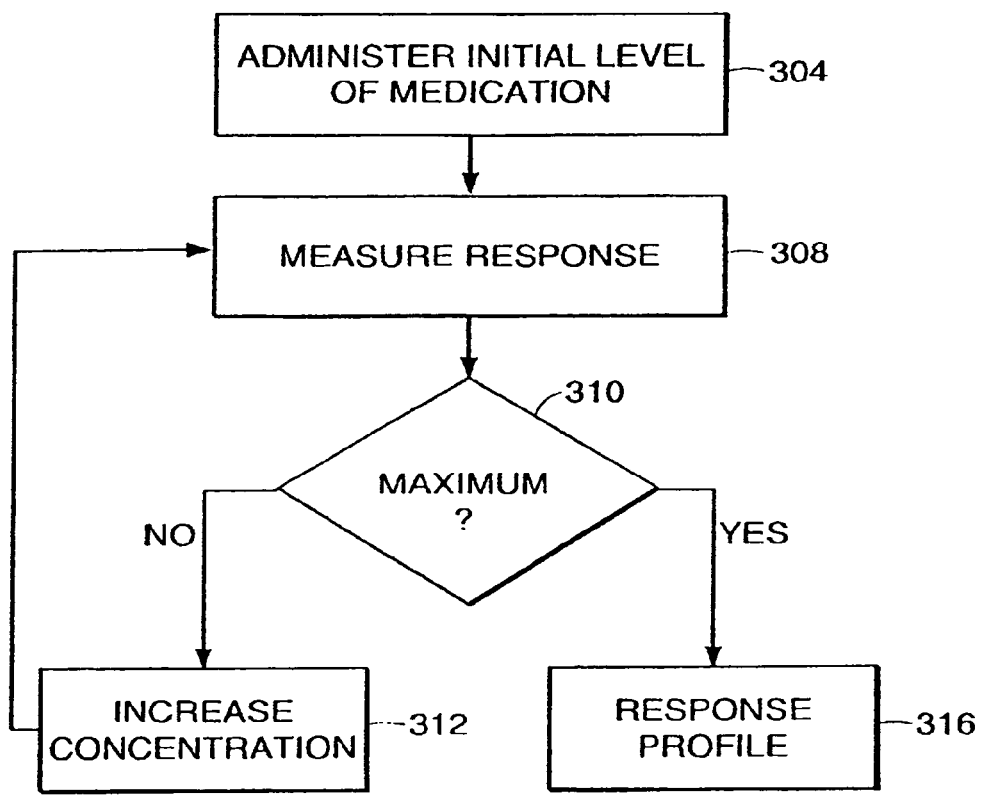
FIG. 3 is an operational flow diagram illustrating a process for determining an initial patient response profile from an unmedicated baseline condition in accordance with one embodiment of the invention.

FIG. 3 is an operational flow diagram illustrating one technique for determining a patient response profile from an unmedicated baseline condition according to one embodiment of the invention. In a step 304, an initial level of medication is administered to the patient. This initial level achieves an initial concentration of medication in the patient's blood stream.

In a step 308, the effect of this initial concentration is measured. In the embodiment illustrated in FIG. 1, the effect of the medication is measured by sensor package 104. Sensor package 104 provides measures to medication delivery controller 108 that can be used to determine or quantify the effect of the medication on patient 116.

In a step 312, the concentration of medication is increased and the effect of this increased concentration is measured in step 308. Preferably, the increase in concentration provided in step 312 is a stepwise increase allowing the effect of specific or quantifiable concentration levels on patient 116 to be measured.

The process of increasing the concentration and measuring the effect of the increased concentration on the patient is repeated until a final concentration level is achieved. This is illustrated by decision step 310. It should be noted that the final concentration level used for the determination in step 310 is preferably a final concentration level required to develop a relatively accurate patient response profile. It is typically not necessary, and more than likely not desirable, that this final concentration level be the maximum level of medication that can be infused into patient 116. The final concentration might also be determined as a certain maximum or safety level reached on the targeted effect.

In a step 316, the measured effects at the various concentration levels are used to calculate the patient response profile. Interpolation and extrapolation can be used to create a complete curve from the obtained data points. Knowledge about the effects of the medication in general can be used for the interpolation and extrapolation. Such knowledge is particularly useful for extrapolation at the maximum concentration levels in the patient.

Figure 4:
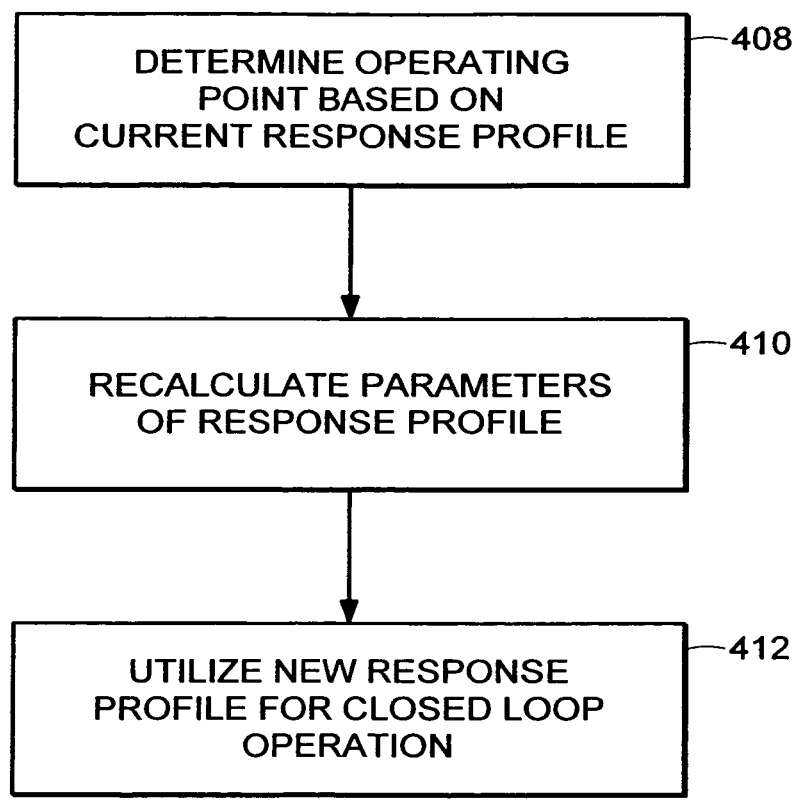
FIG. 4 is an operational flow diagram illustrating a method for adapting the patient response profile in accordance with one embodiment of the invention.

As stated above, in step 220 medication delivery controller 108 adapts to a changing profile to insure that the desired effect is achieved on patient 116. FIG. 4 is an operational flow diagram generally illustrating a process by which the continuous recalculation of the parameters of the patient response profile provide adaptation to changes in the profile in accordance with one embodiment of the invention. In a step 408, medication delivery controller 108 determines a first operating point based on the desired effect and the initial response profile. Specifically, in one embodiment, the current operating point is a level of medication delivery that results in a desired concentration level calculated to achieve the desired effect on patient 116 based on the patient response profile. As the patient response profile changes, in step 410 the parameters of the response profile are recalculated using the effect measures acquired from the sensor package 104, the administered medication concentration and the existing response profile.

In a step 412, the newly recalculated response profile is used by medication delivery controller 108 to ensure that the appropriate concentration of medication is provided to patient 116 by medication delivery unit 112 to achieve the desired effect on patient 116.

Establishing and Adjusting a Patient Response Profile

The patient response profile is the relationship between drug concentration and drug effect, expressed in a mathematical or graphical form. A certain amount of drug being administered to the body is related to the resulting concentration of that drug in the body in a complex manner, due to the pharmacokinetic interactions in the body. During normal procedures, the drug concentration in the body is seldom measured, so the drug concentration in the context of a drug response concentration profile could be a modeled drug concentration when using TCI, or a drug concentration modeled using related concentrations like drug concentration in the exhaled air. Furthermore, it is usual in the pharmacodynamic art to distinguish between a, potentially modeled, blood drug plasma concentration and a modeled theoretical concentration at the site of drug effect. The latter one accommodates for an additional delay in onset of the effect. The use of a patient response profile in the following paragraphs is to be understood to either refer to an infused amount of drug, a steady-state blood plasma drug concentration, or an effect-site concentration. The modeling concepts explained using the response profile can be easily extended to include additional attributes.

Figure 5:
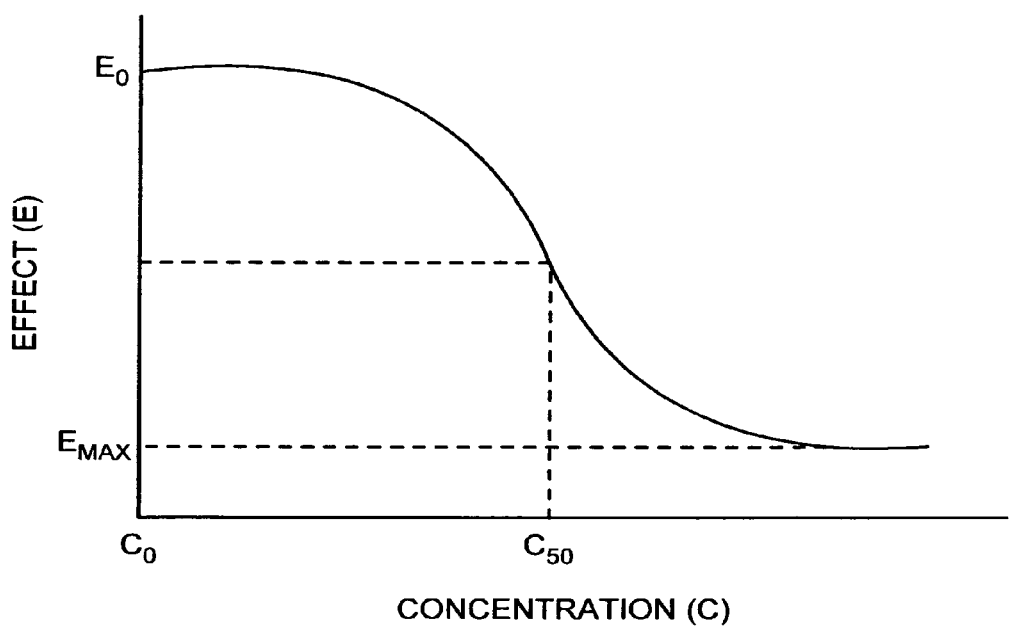
FIG. 5 is a diagram illustrating a patient response profile characterized by an inhibitory sigmoid $E_{max}$ pharmacodynamic model (Hill curve).

Referring now to FIG. 5, it is usual in the pharmacodynamic art to use an inhibitory sigmoid $E_{max}$ pharmacodynamic model to characterize the relationship between steady-state drug concentration (C) and drug effect (E), which ranges from the effect at zero concentration ($E_0$), to the maximum effect, $E_{max}$. In the invention, the effect E is quantified by the Bispectral Index (BIS). In alternate embodiments, other processed EEG measures such as median frequency, spectral edge, entropy metrics and non-EEG measures such as mean arterial pressure may be used alone or in conjunction with the Bispectral Index. The inhibitory sigmoid $E_{max}$ equation, known as the Hill equation, is $$E = E_0 - \frac{E_{max} C^\gamma}{C_{50}^\gamma + C^\gamma} \quad \text{Equation 1}$$

where $\gamma$ is a parameter influencing the slope and sigmoidicity of the curve and $C_{50}$ is the steady-state plasma drug concentration producing half the maximum effect. The preferred embodiment uses the Hill equation as the form of the patient response profile. Using the Hill equation to describe the relationship between the measured effect and the drug concentration, the parameters ($E_0$, $C_{50}$, $E_{max}$, and $\gamma$) of Equation 1 may be estimated for an individual patient or a population of patients. Of these values, the effect at zero drug concentration, $E_0$, may be measured at baseline condition prior to induction (i.e., at C=0). The other parameters of the Hill curve ($E_{max}$, $C_{50}$ and $\gamma$) can be estimated from the measured values of concentration and effect by minimizing the merit function $$\phi = \Sigma (BIS(C)_{sample} - BIS(C)_{Estimated})^2 \quad \text{Equation 2}$$

Here, $BIS(C)_{sample}$ are the set of sampled BIS values corresponding to discrete time points measuring the actual effect at the concentration C and $BIS(C)_{Estimated}$ is a set of predicted BIS values at the same concentration, estimated from the Hill curve equation using the estimated parameters ($E_0$, $E_{max}$, $C_{50}$ and $\gamma$). The optimal set of parameters which fit the data as closely as possible are determined by applying a nonlinear minimization algorithm to the merit function. Throughout the rest of this description, the "(C)" associated with the terms $BIS_{sample}$ and $BIS_{Estimated}$ will be omitted for clarity, but it should be understood that each BIS value is associated with a specific concentration.

The invention applies techniques from Bayesian statistics to the general form of the merit function in Equation 2 to adapt the set of parameters to changes in the patient response profile. The Bayesian method involves assuming an a priori probability function (patient response profile), which may vary from data gained by objective experience to a purely subjective opinion. For statistical inference, the a priori distribution for the unknown parameters is specified. The Bayesian method suggests taking into account common knowledge about results to be expected when deriving conclusions from measurements. In the present invention, the a priori probability function will typically be a population-derived response profile. To permit formal application of the Bayesian approach even when no a priori information is available, a uniform distribution is assumed as an a priori distribution. Using the Bayesian approach, the likelihood function of a sample is multiplied by the a priori probability (density) to obtain the posterior probability (density). The parameter with the highest posteriori probability is then taken as the optimal decision. In this manner, the a priori information is modified by subsequent observations.

Application of Bayesian Forecasting to the Estimation of the Response Profile

The problems of not being able to obtain data during the induction phase relating to the patient's response to high anesthetic agent concentrations and not being able to obtain a patient response profile if the controller is started after the induction phase of surgery may be solved by using Bayesian forecasting. More specifically, a population-derived response profile is used as a starting point. If induction data is available, the low-concentration part of the population-derived response profile may be modified by the lower range anesthetic dose information obtained during the induction. Thus, the patient response data obtained during the induction phase is used to 'tune' the population-derived drug-effect relationship to a specific patient.

Mathematically, one embodiment minimizes the following Hill equation merit function over the induction data:

$$\phi = \sum (BIS_{sample} - BIS_{Estimated})^2 + \\ (E_{0,Population} - E_{0,Estimated})^2 + \\ (E_{max,Population} - E_{max,Estimated})^2 + \\ (c_{0,Population} - c_{0,Estimated})^2 + \\ (\gamma_{Population} - \gamma_{Estimated})^2 \quad \text{Equation 3}$$

The original function to be minimized is extended with 4 terms of the Hill equation, quantifying the 'distance' of our patient-specific response profile from the population-derived response profile. If no induction data points are available, the modeling algorithm will converge to the population-derived response profile, since that will minimize the merit function. If, in contrary, there is a large number of induction data points (say, over a hundred), the modeling algorithm will produce a response profile almost exclusively determined by the measured points.

The initial accuracy of the parameters of the population-derived response profile may vary. In this case, we may want to limit the range throughout which the modeling process can vary the various parameters. This may be achieved by weighting the different parameters by introducing standard deviations for all parameters. We thus obtain $$\phi = \sum \frac{(BIS_{sample} - BIS_{Estimated})^2}{\sigma^2_{samples}} + \frac{(E_{0,Original} - E_{0,Estimated})^2}{\sigma^2_{E_0}} + \frac{(E_{max,Original}, -E_{max,Estimated})^2}{\sigma^2_{E_{max}}} + \frac{(c_{0,Original} - c_{0,Estimated})^2}{\sigma^2_{c_0}} + \frac{(\gamma_{Original} - \gamma_{Estimated})^2}{\sigma^2_{\gamma}}$$

Equation 4

Or, alternatively, $$\phi = \sum \frac{(BIS_{sample} - BIS_{Estimated})^2}{\#samples * \sigma^2_{samples}} + \frac{(E_{0,Original} - E_{0,Estimated})^2}{\sigma^2_{E_0}} + \frac{(E_{max,Original}, -E_{max,Estimated})^2}{\sigma^2_{E_{max}}} + \frac{(c_{0,Original} - c_{0,Estimated})^2}{\sigma^2_{c_0}} + \frac{(\gamma_{Original} - \gamma_{Estimated})^2}{\sigma^2_{\gamma}}$$

Equation 5

These standard deviations might be an estimation of the accuracy of the a priori known values and the sample points, or they may be chosen deliberately in such as way as to influence the way that the optimization algorithm can shift the parameters away from their original values, thus in effect influencing the way the curve is shaped for this specific patient. If we make the $\sigma^2$ very large, the corresponding parameter will be easily modified by the optimization algorithm. If it is very small, a slight difference from the starting value will generate large values in the evaluation of the merit function, thus effectively limiting a change in this parameter.

Several other features from the curve or its estimation in the merit function may be introduced to control the variation of the Hill curve parameters during the modeling process. We may, for example, determine that the range of the curve, being ($E_0-E_{max}$), can only be modified slightly. This may be accomplished by adding the following term to the sum in Equation 5 to be minimized:

$$\frac{((E_{0,Original} - E_{max,Original}) - (E_{0,Estimated} - E_{max,Estimated}))^2}{\sigma^2_{DeltaELow}}$$

(Equation 6)

or $$\frac{(E_{0,Original} - E_{max,Original} - E_{0,Estimated} + E_{max,Estimated})^2}{\sigma^2_{DeltaELow}}$$

where $\sigma^2_{DeltaELow}$ would then be very small.

In addition, terms specifically influencing particular parameters based upon the data measurement may be added to the merit function. For example, wobble or divergence in the measured points might be introduced to specifically correct one parameter by introducing a term which would, for example, link variations in successive sampled BIS values to the Hill curve slope:

$$\frac{\left(\sum \frac{(BIS_{sample,t} - BIS_{sample,t-1})^2}{\#samples} - \gamma\right)^2}{\sigma^2_{sample\_\gamma}}$$

Equation 7

Many other methods of modifying the merit function will be obvious to those skilled in the art. These examples are not intended to be a comprehensive list.

The advantage of this method is that it allows the simultaneous estimation of all parameters using different boundaries or restrictions. This is in contrast to other methods of applying several equations or different estimating methods in which repeated iterations are required to have one parameter fit several restrictions. Of course, it is still possible to use the least-squares method or any other method to derive the parameters in a separate equation as well, as we did for the $E_0$.

Adaptation of Hill Curve Parameters to a Changing Patient Response Profile—Time-Limiting Factors Another application of Bayesian forecasting is to modify the Hill curve parameters to adapt to changes in the patient's response profile during surgery. This change may be the result of the waning effect of premedication that was active during induction, or due to other physiological phenomena happening in the patient during surgery. An important component of this application is the selection of the set of parameters the algorithm may modify during surgery and to what degree. In addition, since the value of sampled data decreases with increasing sample age, another important factor is determining the relative weighting to be applied to data of varying age.

In general, the previous merit functions may be extended with additional terms, yielding the following general sum to be minimized:

$$\phi = \sum \frac{(BIS_{sample} - BIS_{Estimated})^2 * e^{\frac{(t-t_{sample})}{sample\_half\_life}}}{\sigma^2_{samples}} + \frac{(E_{0,Original} - E_{0,Estimated})^2}{\sigma^2_{E_0}} + \frac{(E_{max,Original}, -E_{max,Estimated})^2}{\sigma^2_{E_{max}}} +$$

Equation 8

$$+ \frac{(c_{0,Original} - c_{0,Estimated})^2}{\sigma_{c_0}^2} +$$

$$\frac{(\gamma_{Original} - \gamma_{Estimated})^2}{\sigma_\gamma^2}$$

Equation 8 restricts in time the influence of measured data, by introducing a so-called 'time-limiting factor'. We do not want, for example, induction data to remain equally relevant throughout the surgery. The constant sample_half_life is chosen to define the rate of decline of the time-limiting factor and thus of the relative influence of samples of varying ages. In the preferred embodiment, sample_half_life=600 seconds.

The exponential form of this time-limiting factor results in a very steep initial decay, with a long "tail". As a result, the most recent samples have a very strong influence; as the samples age, their influence decreases, though they maintain some influence for a very long time. The influence of the various time samples may be modified through the use of a different time-limiting factor, which applies an absolute time limit on the age of samples included in the modeling process:

$$\phi = \sum \frac{(BIS_{sample} - BIS_{Estimated})^2 * \left(1 - \left[\frac{(t-t_{sample})}{sample\_half\_life}\right]^2\right)}{\sigma_{samples}^2} +$$

$$\frac{(E_{0,Original} - E_{0,Estimated})^2}{\sigma_{E_0}^2} +$$

$$\frac{(E_{max,Original}, - E_{max,Estimated})^2}{\sigma_{E_{max}}^2} +$$

$$\frac{(c_{0,Original} - c_{0,Estimated})^2}{\sigma_{c_0}^2} +$$

$$\frac{(\gamma_{Original} - \gamma_{Estimated})^2}{\sigma_\gamma^2}$$

Equation 9

The summation algorithm is implemented such that if the time-limiting factor for a particular sample is less than 0, it is no longer entered into the sum. This calculation has several advantages:

- it emphasizes more recent datapoints, in contrast to the exponential decay which falls down rapidly.
- it requires a multiplication, instead of an exponential calculation.
- the relative weighting applied to any particular sample is 1 at the time of the sample, and 0 at time=sample_half_life.
- The contribution of sample points in the sum is finite, so the calculations are computed faster.

The incorporation of a time-limiting factor allows the use of even larger terms in the merit function. For example, recent data points may be used to tune curve slope, or extreme measured points may be used to tune the maximum and minimum curve values.

For curves expected to be log normally distributed, an alternative merit function may be specified as $$\phi = \sum \frac{(\ln(BIS_{sample}) - \ln(BIS_{Estimated}))^2 * e^{\frac{(t-t_{sample})}{sample\_half\_life}}}{\sigma_{samples}^2} +$$

$$\frac{(\ln(E_{0,Original}) - \ln(E_{0,Estimated}))^2}{\sigma_{E_0}^2} +$$

$$\frac{(\ln(E_{max,Original}) - \ln(E_{max,Estimated}))^2}{\sigma_{E_{max}}^2} +$$

$$\frac{(\ln(c_{0,Original}) - \ln(c_{0,Estimated}))^2}{\sigma_{c_0}^2} +$$

$$\frac{(\ln(\gamma_{Original}) - \ln(\gamma_{Estimated}))^2}{\sigma_\gamma^2}$$

Equation 10

This technique allows the adaptation of the Hill curve parameter to changes in the patient's response profile.

Minimization of the Merit Function: The Levenberg-Marquardt Method

The sample data $y_i$ (consisting of N samples, either sampled during induction or during surgery) must be fitted to the Hill curve model y, which depends nonlinearly on the set of M unknown parameters ($E_0$, $E_{max}$, $C_{50}$, $\gamma$) and where $x_i$ is the set of concentration values. To obtain a maximum likelihood optimization, we define a $\chi^2$ merit function and determine the best-fit parameters by its minimization.

$$\chi^2 = \sum_{i=1}^{N} \left(\frac{y_i - y(x_i; E_0; E_{max}; \gamma; C_{50})}{\sigma_i}\right)^2$$

Equation 11

This approach can be used with any model. Unfortunately, in the case of non-linear dependencies, the minimization of $\chi^2$ must proceed iteratively. Beginning with a set of initial parameter values, we develop a procedure that improves the initial solution. The procedure is then repeated until $\chi^2$ stops (or effectively stops) decreasing, providing the maximally likely parameters.

The goodness of fit of the maximum likelihood model can be calculated using the following procedure. If we assume that the measurement errors are normally distributed, $\chi^2$ is a sum of N squares of normally distributed quantities, each normalized to unit variance. Even though after optimization, the terms in the sum are no longer linearly independent, the probability distribution for different values of $\chi^2$ at its minimum is the chi-square distribution for N-M degrees of freedom. This is assumed to hold true even for models that are not strictly linear in the parameters.

Thus, having the degrees of freedom ν (number of sample points minus the number of parameters to be estimated) and the resulting $\chi^2$ value, we can calculate the probability Q that the chi-square (error) is larger than the calculated $\chi^2$ value (and thus, the goodness of fit) by using a chi-square distribution calculation with the resulting values.

$$Q = gamma(0.5\nu, 0.5\chi^2)$$

Equation 12

It is important to note that, since $\chi^2$ is dependent on the assumed standard deviations of the sample points, this standard deviation should be estimated accurately, in order to obtain a reliable goodness-of-fit. The goodness of fit may be used as a decision criteria, deciding whether the quality of the estimate is great enough to use the response profile in closed loop operation and thus as the subsequent initiate for the next iteration of the response profile update.

A common method of implementing the minimization of non-linear functions is the Levenberg-Marquardt method. This method is described in detail in Press, et al., *Numerical Recipes in C: The Art of Scientific Computing*, 2$^{nd}$ Edition. Cambridge University Press, New York, N.Y., 1992, Chapter 15.5. This description therefore provides only the specific solution and omits the intermediate steps.

Given the $\chi^2$ merit function $$\chi^2(a) = \sum_{i=1}^{N} \left(\frac{y_i - y(x_i; a)}{\sigma_i}\right)^2 \qquad \text{Equation 13}$$

where a is the set of Hill curve parameters, we apply the Levenberg-Marquardt method. We obtain the set of parameters a that minimizes the merit function $\chi^2$ by solving the set of simultaneous equations $$\sum_{i=1}^{N} \alpha'_{kl} \Delta a_l = \beta_k \qquad \text{Equation 14}$$

where $$\beta_k \equiv -\frac{1}{2} * \frac{\partial^2 \chi^2}{\partial a_k} \qquad \text{Equation 15}$$

$$\alpha_{kl} \equiv \frac{1}{2} * \frac{\partial^2 \chi^2}{\partial a_k \partial a_l}$$

and $$\alpha'_{jj} \equiv a_{jj} * (1 + \lambda) \qquad \text{Equation 16}$$

$$\alpha'_{jk} \equiv a_{jk}; (j \neq k)$$

Given an initial guess for the set of fitted parameters a, the Levenberg-Marquardt procedure is as follows:
1. Compute $\chi^2$ (a).
2. pick a modest value for $\lambda$, say 0.001.
3. Solve the set of linear Equation 14 for $\Delta a$ and evaluate $\chi^2(a+\Delta a)$.
4. If $\chi^2(a+\Delta a) \geq \chi^2(a)$, increase $\lambda$ by a factor of 10 (or any other substantial factor) and go back to (3).
5. If $\chi^2(a+\Delta a) < \chi^2(a)$, decrease $\lambda$ by a factor of 10, update the trial solution a←a+$\Delta a$, and go back to (3).

It is necessary to specify a condition for stopping. Iterating to convergence (to machine accuracy or to the round-off limit) is generally wasteful and unnecessary since the minimum is at best only a statistical estimate of the parameters a. The preferred embodiment defines a stopping condition as being fulfilled when the absolute percent change in $\chi^2$ from the previous step to the current step is less than 0.1%; that is $$\left|\frac{(\chi^2(a + \Delta a) - \chi^2(a))}{\chi^2(a)}\right| < 0.001 \qquad \text{Equation 17}$$

and the new $\chi^2$ is not less than the previous value. This condition is evaluated at the end of step 3.

Extension of the Levenberg-Marquardt Method to Incorporate A Priori Values

The sample data (either sampled during induction, or during surgery) is again fitted to the Hill curve model, which depends nonlinearly on the set a of M unknown parameters ($E_0$, $E_{max}$, $C_{50}$, $\gamma$). As with the general Levenberg-Marquardt method, we define a merit function $\chi^2$ and determine the best-fit parameters by its minimization, but in contrast to the previously described algorithm which starts from unknown parameter values, for the Bayesian adaptation we will start from known values for these parameters. This process is robust; the known values are considered reliable and the optimized parameter values can vary significantly from the preset values if there are a sufficient number of sample points to ensure high confidence.

The merit function is similar to that of the typical Levenberg-Marquardt method; however, additional terms are incorporated similar to those described in Equation 4. Specifically, assume that we want to impose the following additional requirements:

$$\chi^2 = \sum_{i=1}^{N} \left(\frac{y_i - y(x_i; E_0; E_M; \gamma, C_{50})}{\sigma_i}\right)^2 + (E_0 - E_0^{ori})^2 + \qquad \text{Equation 18}$$

$$(E_{max} - E_{max}^{ori})^2 + (C_{50} - C_{50}^{ori})^2 + (\gamma - \gamma^{ori})^2$$

where the current parameter set a=($E_0$, $E_{max}$, $C_{50}$ and $\gamma$) and the original parameter set $a^{ori}$=($E_0^{ori}$, $E_{max}^{ori}$, $C_{50}^{ori}$ and $\gamma^{ori}$).

We first introduce a weighting factor, which we will call variability. The variability is to be distinguished from the variance or standard deviation of the parameter. The earlier determined population-derived known standard deviations of the parameter results from the original estimation circumstances. Weighing each parameter's contribution in the merit function on its standard deviation equalizes their contribution in the merit function. Still, we may want to enable the minimization routine to select values differing from the original values more easily for certain parameters than others. This can be achieved, starting from the equally-weighed contribution in the merit function, by adding a multiplicative term in the denominator for that specific parameter. The variability is thus defined as the variance multiplied with an optional factor. In this way, we can consider the original parameter values as input data of the same kind. The variability is simply a parameter that will, eventually, influence the variance on the calculated parameters. We might use any previously determined population-derived known variances on the parameters as a guideline to set the variability in this case.

$$\chi^2 = \sum_{i=1}^{N} \left(\frac{y_i - y(x_i; E_0; E_M; \gamma; C_{50})}{\sigma_i}\right)^2 + \left(\frac{E_0 - E_0^{ori}}{\text{var}_{E_0}}\right)^2 + \qquad \text{Equation 19}$$

$$\left(\frac{E_{max} - E_{max}^{ori}}{\text{var}_{E_{max}}}\right)^2 + \left(\frac{c_{50} - c_{50}^{ori}}{\text{var}_{C_{50}}}\right)^2 + \left(\frac{\gamma - \gamma^{ori}}{\text{var}_{\gamma}}\right)^2$$

or $$\chi^2 = \sum_{i=1}^{N} \left(\frac{y_i - y(x_i; [a])}{\sigma_i}\right)^2 + \frac{[a - a^{ori}]}{[\sigma_a]} * \frac{[a - a^{ori}]^T}{[\sigma_a]^T}$$

The Levenberg-Marquardt optimization method is similar to that described above except that Equation 15 now becomes $$\alpha_{kl} \equiv \frac{1}{2} * \frac{\partial^2 \chi^2}{\partial a_k \partial a_l} \equiv \sum_{i=1}^{N} \frac{1}{\sigma_i^2} \left[ \frac{\partial y(x_i; a)}{\partial a_k} * \frac{\partial y(x_i; a)}{\partial a_l} \right] + \frac{\delta_{kl}}{\sigma_{a,k} \sigma_{a,l}} \quad \text{Equation 20}$$

$$\beta_k \equiv -\frac{1}{2} * \frac{\partial^2 \chi^2}{\partial a_k} \equiv \sum_{i=1}^{N} \frac{y_i - y(x_i; a)}{\sigma_i^2} * \frac{\partial y(x_i; a)}{\partial a_k} - \frac{[a_k - a_k^{ori}]}{\sigma_{a,k}^2}, \quad \text{Equation 21}$$

Minimization of Hill Curve Models with Time-Limiting Factors

The minimization of the merit function in Equation 9 may also be accomplished using the Levenberg-Marquardt method. The time-limiting factor will limit the number of samples that are taken into account for the merit function as a function of their age. In addition, a gradually decreasing importance will be awarded to the sample points with increasing sample age. The time-limiting factor to be applied has to be chosen carefully: we want a gradual decrease of importance awarded to the data points in the merit function. The most recent data point will be awarded a value of 1, whereas the last data point to take into account has a value of zero. The intermediate data points will have a relevance corresponding to the following function:

$$\left(1 - \left[\frac{(t - t_{sample})}{\text{sample\_half\_life}}\right]^2\right) \quad \text{Equation 22}$$

The merit function (Equation 19) now becomes:

$$\chi^2 = \sum_{i=1}^{N} \left(\frac{y_i - y(x_i; [a])}{\sigma_i}\right)^2 * \left(1 - \left[\frac{(t - t_{sample})}{\text{sample\_half\_life}}\right]^2\right) + \quad \text{Equation 23}$$

$$\frac{[a - a^{ori}]}{[\sigma_a]} * \frac{[a - a^{ori}]^T}{[\sigma_a]^T}$$

Note that Equation 23 is implemented such that the summation over the samples ends when $(t - t_{sample}) > \text{sample\_half\_life}$. Since the number of data points taken into account is always limited, we can now better balance the contributions of the sample data points and the deviation of the parameters in the merit function.

We can determine an equivalent multiplier for the sum over the data points with decreasing relevance, assuming that we have one data point per second:

$$MUL = \sum_{i=0}^{\text{sample\_lifetime}} \left(1 - \left[\frac{(t - t_{sample})}{\text{sample\_half\_life}}\right]^2\right) \cong \quad \text{Equation 24}$$

$$0.5 - \frac{1}{6 * \text{sample\_half\_life}} + \frac{2 * \text{sample\_half\_life}}{3}$$

This 'equivalent multiplier' can be used to weight the number of data points. Equation 23 can be rewritten:

$$\chi^2 = \quad \text{Equation 25}$$

$$\sum_{i=1}^{N} \left(\frac{y_i - y(x_i; [a])}{\sigma_i}\right)^2 * \left(1 - \left[\frac{(t - t_{sample})}{\text{sample\_half\_life}}\right]^2\right) * \frac{1}{MUL} +$$

-continued $$\frac{[a - a^{ori}]}{[\sigma_a]} * \frac{[a - a^{ori}]^T}{[\sigma_a]^T}$$

At steady-state and with at least sample_half_life data points at a data acquisition rate of one per second, the weighted contribution of the sample data points is equivalent to that of the parameters' deviance. In the case of a smaller set of available data, the contribution of the parameters deviance is more important. Mathematically, the introduction of the term MUL and the time-limiting factor does not significantly change the optimization algorithm: the combination of both can be considered a sample-specific variance.

Concerning the accuracy of the best fit, we can consider the combination of the samples with their 'corrected' variance as one single sample. This means we can still use the gammq function, albeit using one degree of freedom instead of the number of samples. If we don't have exactly sample_half_life samples in the sum, the obtained accuracy will be too optimistic, since the result of the merit function will be smaller.

Embodiments of the Invention in Anesthetic Drug Applications

As described above, one application of the invention is in the environment of the delivery of an anesthetic to achieve a desired level of sedation, or sedation effect, on a patient. One or more embodiments of the invention are now described in terms of this example environment. There are a number of measures that can be used individually or in combination to monitor the effects of an anesthetic drug on a patient. One parameter, the Bispectral Index, can be used to measure the hypnotic effect of an anesthetic on cerebral activity.

In one embodiment of the invention, a bispectral analysis of the patient's EEG signal is used as a method for monitoring the hypnotic (sedative) effect of an anesthetic drug on the patient. Through the identification of predictive and correlative features in, among others, the EEG bispectrum and the time-domain level of burst suppression, a multivariant parameter can be calculated referred to as the Bispectral Index® (BIS®). The Bispectral Index is a quantifiable parameter well known in the art. The Bispectral Index is described in U.S. Pat. No. 5,792,069 (which is incorporated herein by reference) and has been integrated into the bispectral EEG monitors such as those available from Aspect Medical Systems, Inc., of Newton, Mass., USA. The Bispectral Index is utilized by medication delivery controller 108 to determine whether the desired effect, i.e., level of sedation, has been achieved for a patient.

Because the combination of the EEG and hemodynamics may prove to be more adequate in monitoring the depth of anesthesia than a single parameter, both hemodynamics and the Bispectral Index can be used as measures in the closed-loop system according to one embodiment of the invention. As stated above, it is often a goal of a medication delivery system to achieve and maintain a desired effect on the patient. This desired effect or level of effect can be referred to as the set point, or target value. The set point specified by the anesthetist or other health care professional is preferably approached and maintained as closely as possible during the maintenance of the anesthesia or sedation. Preferably, in one embodiment, set points for the different variables to be controlled can be offered to the health care professional as the values measured after induction, in a quiet state before intubation. The set points can be changed according to clinical needs during the course of the procedure or treatment of the patient.

Figure 6:
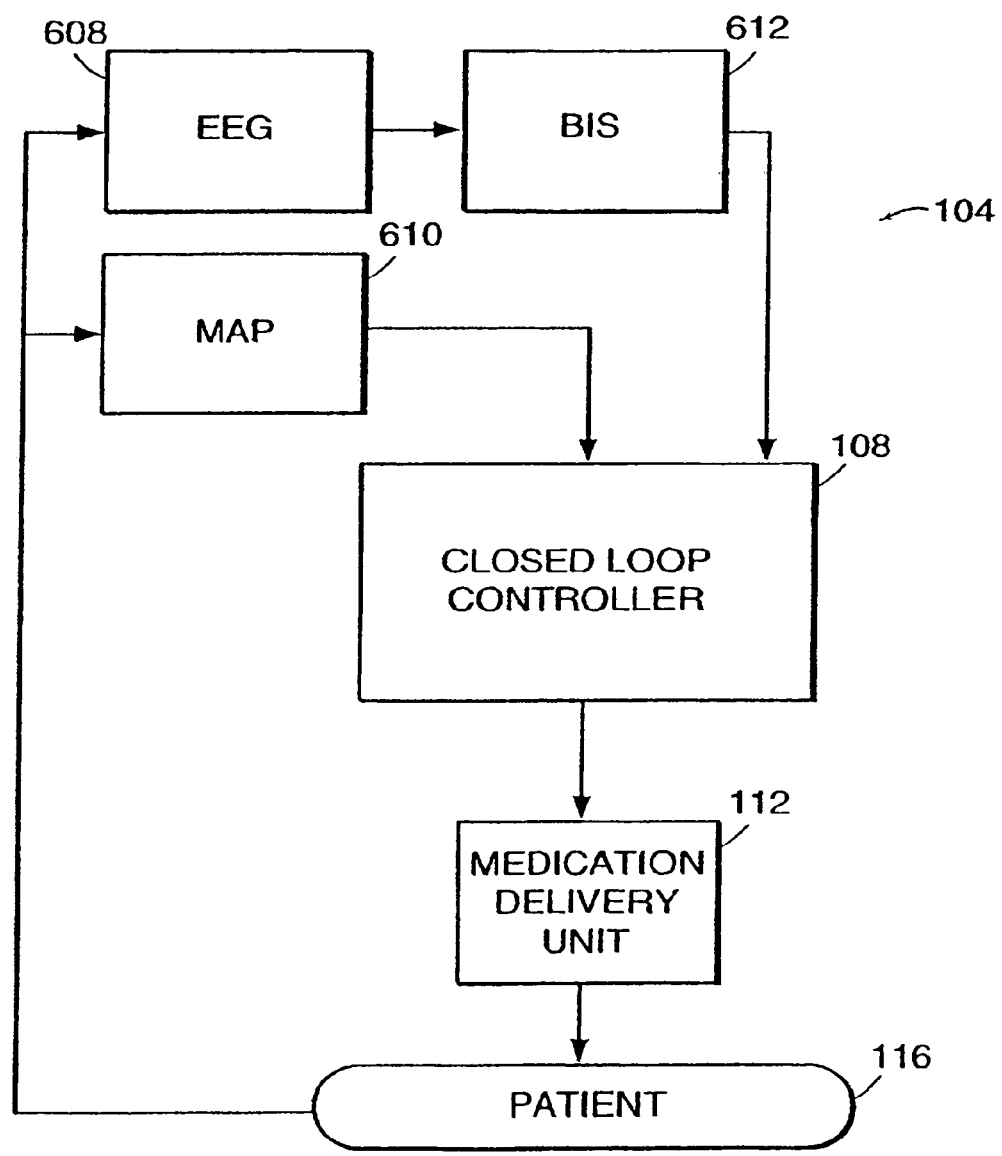
FIG. 6 is a block diagram illustrating an application of the invention suitable for use in the administration of anesthetic medications in accordance with one embodiment of the invention.

FIG. 6 is a block diagram illustrating an example implementation of a medication delivery controller 108 and an anesthetic drug delivery environment that utilizes mean arterial pressure and Bispectral Index as measures of effect in the closed-loop delivery system. Referring now to FIG. 6, as illustrated in this example embodiment, sensor package 104 includes an EEG monitor 608 and a Bispectral Index device 612. As illustrated in FIG. 6, patient 116 is connected to EEG monitoring device 608. Preferably, EEG monitoring device 608 is configured to accept EEG data and perform calculations to obtain processed EEG data. The processing can include a determination of a Bispectral Index, a suppression ratio, and artifact information which are provided to medication delivery controller 108. Sensor package 104 also includes a measurement device 610 for determining mean arterial pressure (MAP) that is also provided to medication delivery controller 108. These measures of effect can be provided to medication delivery controller 108 via a hardwired or wireless communications interface such as, for example, an RS-232 interface and are used as correlates of drug effects. The Bispectral Index is used as a controlled variable while, in one embodiment, the suppression ratio and artifact information are used as safety measures. In an alternative embodiment, other signals (EEG or evoked potential (EP)) may be used as a controlled variable, as well as other processed measures computed from these signals such as EEG spectral edge, median frequency and absolute and relative EEG power within various frequency bands.

Figure 7:
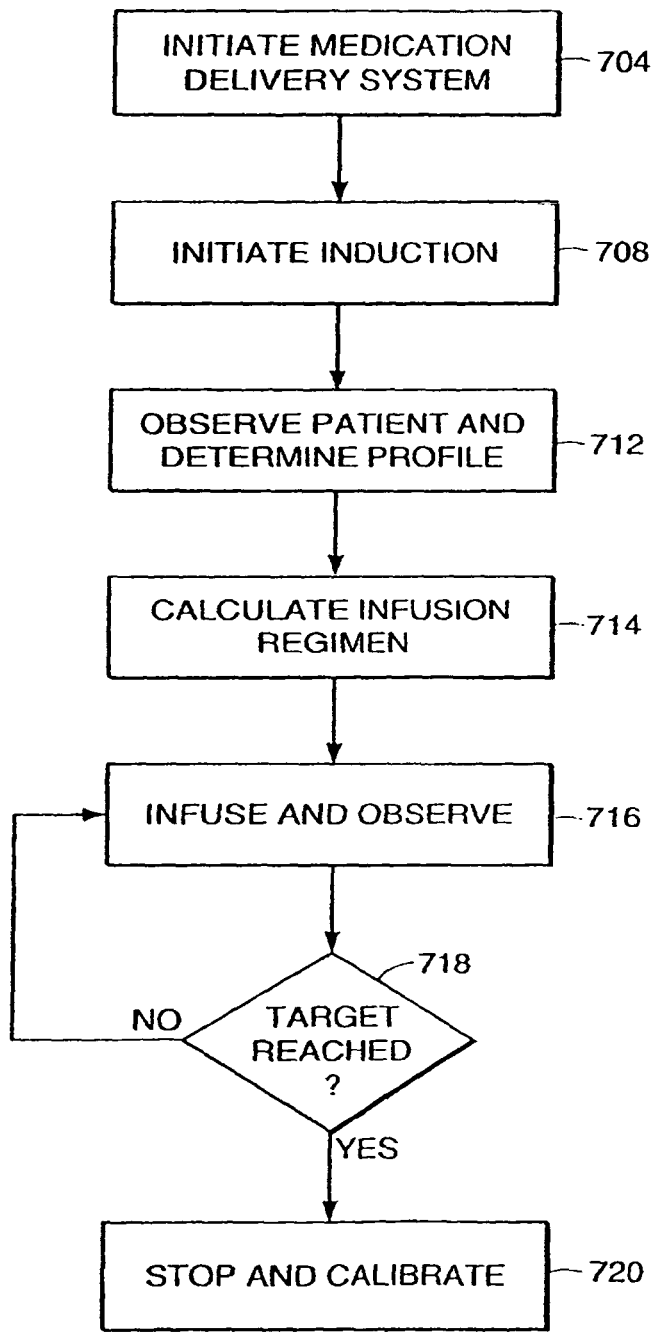
FIG. 7 is an operational flow diagram illustrating the operation of a medication delivery controller in the example environment of the administration of anesthetic medication in accordance with one embodiment of the invention.

FIG. 7 is an operational flow diagram illustrating the operation of medication delivery controller 108 in this example environment in accordance with one embodiment of the invention. In a step 704, the medication delivery system is initiated. Preferably, in this step, patient individual anthropometric data, such as, for example, weight, age, height and gender are entered. Additionally, at this step, the target Bispectral Index and safety values (e.g., suppression ratio limit, MAP limits, etc.) can be entered. Preferably, the system is initiated prior to induction of the patient. Additionally, the anesthetist sets the initial effect-site concentration. The anesthetist or other clinician can enter this initial data by manual entry using a user-interface as described in more detail below. Additionally, this data can be entered by a communications interface, such as, for example, by local area network or other communications, provided this information is available for retrieval by this medium.

In a step 708, the process of induction is initiated. In a step 712, during the induction, medication delivery controller 108 observes the patient's response to a specific effect-site concentration of the anesthetic using the various measures of effect, such as Bispectral Index, MAP, etc. This observation is performed to enable the medication delivery controller 108 to calculate the patient's individual response profile. In the case of an anesthetic drug, the response profile is, in one embodiment, a pharmacodynamic Hill curve. The large pharmacodynamic variability that is present among patients can cause error when using a combined pharmacokinetic-pharmacodynamic model. This means that using mean population pharmacokinetic as well as mean population pharmacodynamic values for a particular dosage regimen may result in significant dosage error in any individual patient. The probability of this error occurring can be minimized or at least reduced by utilizing individualized Hill curves to adjust the delivery of the anesthetic drug. For this reason, the preferred embodiment calculates an individualized Hill curve, which is used as the patient response profile and is used to adjust the delivery of the anesthetic drug. Specifically, in one embodiment, medication delivery controller 108 initiates an induction at a specific effect-site concentration of anesthetic that is preferably set by the anesthetist. This concentration is increased automatically at periodic intervals with predefined steps. For example, in one embodiment, the concentration is automatically increased every minute with a stepwise increase of 0.5 micrograms/milliliter. This step is referred to as effect-site controlled open-loop drug delivery using population pharmacokinetic modeling. Pharmacokinetic modeling is well known in the anesthesia art. At each concentration level in step 712, the measure of effect (e.g., BIS) is observed. The resultant series of paired concentration and effect data are used in step 712 to calculate an initial individualized patient response profile.

In a step 714, medication delivery controller 108 calculates an infusion regimen to reach the specified effect-site concentration. The infusion regimen, which can be calculated in terms of a bolus and a maintenance infusion, can be specified in ml/hour and used to steer medication delivery unit 112 in the delivery of medication to patient 116. During infusion, medication delivery controller 108 observes the effect measures. If the target Bispectral Index is reached, the increase in effect-site concentration is stopped and controller 108 automatically calculates the Hill curve. Thereafter, medication delivery controller 108 switches automatically from open-loop control to closed-loop control. Steps 718 and 720 illustrate this.

In a closed-loop operation, medication delivery controller 108 operates in the adaptive closed-loop mode, recalculating the Hill curve in response to changing patient condition in order to achieve the desired level of sedation with patient 116.

In an alternate embodiment, a population-based response profile is used in place of the individually-determined response profile calculated in step 712. If induction response data is available, the Bayesian method may be used to modify the Hill curve parameters as previously discussed. The Bayesian method may then be used during closed loop operation to adapt the parameters of the response curve to changing patient state. This allows the use of the drug delivery system in instances where the induction data is unavailable or is considered unreliable, due to patient characteristics, such as underlying disease or adverse physical condition. Again, the shape of the patient response curve can change to adapt to changing patient condition.

Medication Delivery Controllers

Medication delivery controller 108 can be implemented utilizing a variety of different technologies in a variety of different architectures to achieve the desired result. As stated above, a primary purpose of a medication delivery controller 108 is to sense the resultant effect on patient 116 by the measures of effect from sensor package 104 and to adjust the medication delivery rate to achieve the desired result. Preferably, a microprocessor-based software-controlled device is utilized to perform this function. The microprocessor-based device includes an input interface to receive measures from sensor package 104 and an output interface to provide control information to medication delivery unit 112.

Figure 8:
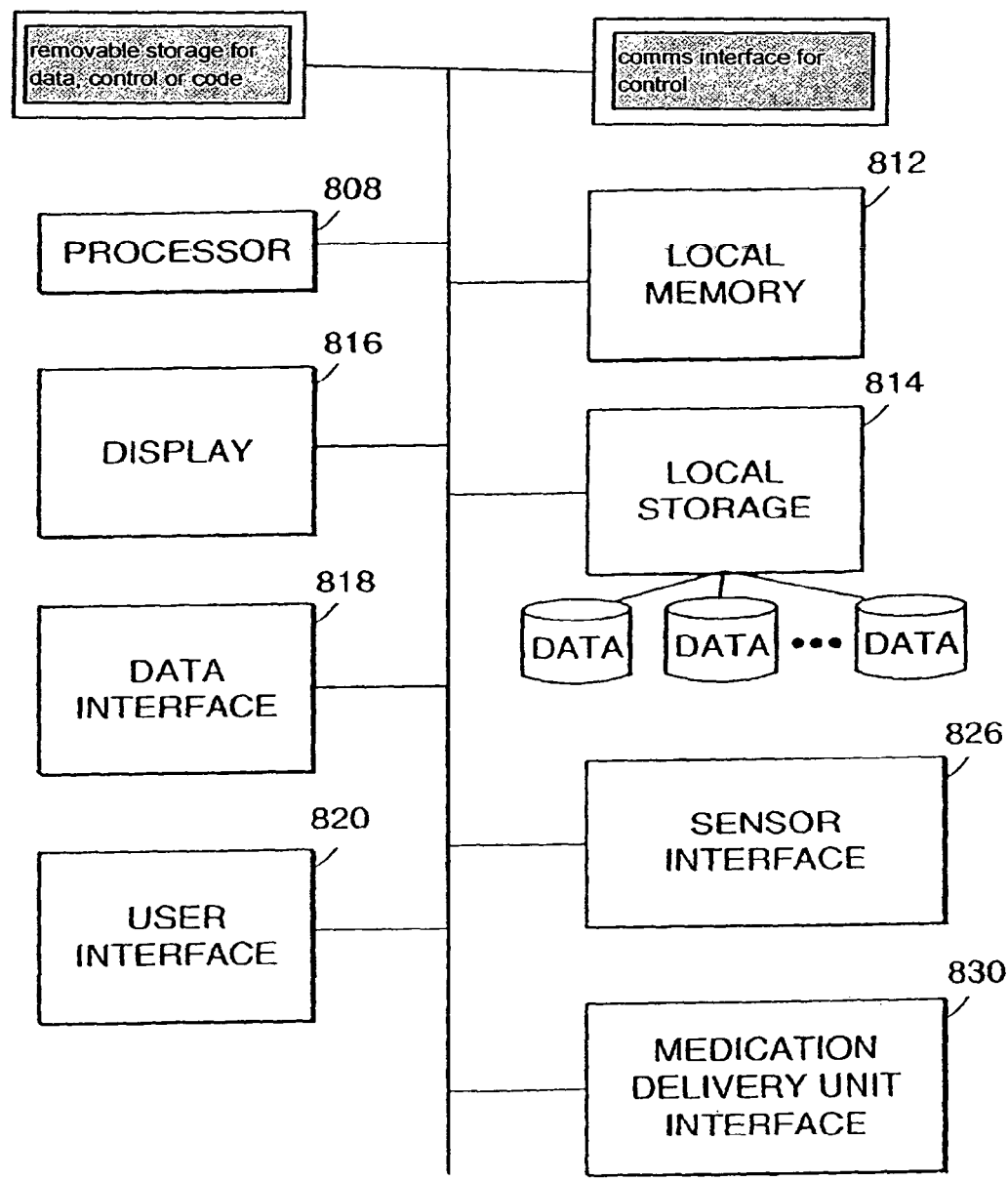
FIG. 8 is a block diagram illustrating an example architecture of a medication delivery controller in accordance with one embodiment of the invention.

As will be appreciated by one of ordinary skill in the art after reading this description, there are a number of devices and/or architectures that can be implemented to perform these functions. One such example architecture is illustrated in FIG. 8. The example architecture illustrated in FIG. 8 includes a microprocessor 808, local memory 812, a sensor interface 826, and a medication delivery unit interface 830.

Microprocessor 808 can be implemented utilizing a variety of different microprocessor types including, for example, the X86 family of microprocessors or a Pentium® microprocessor.

Local memory 812 can include random access memory (RAM) and read-only memory (ROM). Local memory 812 can be used to store program instructions that control microprocessor 808, values or other variables used in operation of microprocessor 808 in executing the program instructions, and results of the operation of medication delivery controller 108.

Sensor interface 826 and medication delivery unit interface 830 are included to provide interfaces to sensor package 104 and medication delivery unit 112, respectively. Interfaces 826, 830 can be implemented using hardwired or wireless interfaces. A variety of communications standards can be used such as, for example, RS-232, RS-422, or any of a number of alternative communications standards or protocols.

Additionally, features can be included in the architecture of medication delivery unit 108 to provide enhanced or additional functionality. These additional features can include, for example, a display 816, a data interface 818, a user interface 820 and local storage 814. Various embodiments of each of these additional components are now described. Display 816 can be included to provide information to an anesthetist or other clinician utilizing medication delivery controller 108. Display 816 can be implemented using conventional technology and can be implemented as, for example, an LCD or a CRT display. Display 816 can be implemented as a simple text-only display providing the user with one or more lines of text informing the user of the status or current operation being performed by medication delivery controller 108. Alternatively, display 816 can be implemented as a more conventional computer display offering text and graphics to the user such as that found on many Windows®-based personal computers. In fact, in one embodiment, the software utilized to control medication delivery controller 108 is a software package designed to operate on the Windows® operating system. Display 816 can also be implemented as a touch-screen display to facilitate user input. Alternative display devices or configurations can also be used, depending on the application.

User interface 820 can be included to provide the user with a means for inputting user data to medication delivery controller 108. User interface can include, for example, a keyboard or keypad, a pointing device such as a mouse or other pointing device and an encoded label reader. Examples of an encoded label reader can include, for example, bar code label readers, magnetic stripe readers, OCR readers or other code reading devices. User interface 820 can be used by the clinician to provide data used by medication delivery controller 108 in its operation as well as to control or otherwise alter the operation of medication delivery controller 108. As stated above, an operator can enter patient attributes such as height, weight, age, and gender into medication delivery controller 108. User interface 820 can be provided to facilitate such entry.

A data interface 818 can also be included to allow medication delivery controller 108 to access data from or provide data to other entities or devices. For example, patient attributes or other data may be available to medication delivery controller 108 via an external database or other external source. Data interface 818 can be utilized as a conduit for providing this data to medication delivery controller 108. In one embodiment, data interface 818 can be implemented using a network interface to allow medication delivery controller 108 to provide information to or access information from one or more databases or other entities on a computer network. Data interface 818 can be implemented as a hard-wired or a wireless interface.

Preferably, medication delivery controller 108 is implemented as a fixed or transportable device rather than a portable device. Therefore medication delivery controller 108 is designed to be plugged into an A/C wall outlet. However, alternative embodiments can be implemented wherein medication delivery controller 108 is operated by batteries or other portable or transportable independent power source. Of course, the selection of components, especially, for example, the display, may be made based on power consumption and heat dissipation characteristics.

Additionally, a local storage device 814 can be included to provide storage for data or additional storage for program instructions. Local storage 814 can, for example, be implemented as a disk drive or other storage device. Local storage 814 can be used to store a variety of patient data or medication data as well as for storing a history of the operations performed by medication delivery controller 108.

As stated above, there are numerous alternative architectures that can be implemented to provide the functionality of medication delivery controller 108. The examples discussed above with reference to FIG. 8 are provided by way of example only. After reading this description it will become apparent to one of ordinary skill in the art how to implement medication delivery controller 108 using a number of alternative architectures and components.

As discussed, medication delivery controller 108 determines delivery parameters for the medication based on the response profile determined. In one embodiment, the delivery parameter determined is a required infusion rate. The infusion rate of a medication can be calculated by a straightforward mathematical formula based on the difference between the measured value and the chosen target value set by the user. Conventional controllers often operate without knowledge of the drug metabolism and the realized concentration values. Without fine-tuning for a specific situation, these conventional controllers can be slow to establish control and become dangerous to use because of possible oscillations. Furthermore, fine tuning of conventional controllers is difficult as the human body and its responses to medication is very complex. As a result, this may lead to clinical difficulties due to the complex pharmacologic behavior of products used, inter-individual pharmacologic variability and patient's reactions to external stimuli.

A model-based controller may be used to control the administration of drugs in response to clinical effects where the control is based on knowledge of the drug and its effect in the human body based on a mathematical model. In a preferred embodiment, a model-based adaptive controller is utilized which compares the output predicted by the model to actual output values in order to adjust the model parameters for the individual. According to a preferred embodiment of the invention, medication delivery controller 108 calculates a target concentration value for a TCI (Target Controlled Infusion) system that steers for this concentration by calculating the corresponding infusion regimen. Using a TCI system, the input-output complexity can be reduced. In other words, if the system can immediately steer the blood or effect-site concentration, instead of the pump rate, third order behavior of the anesthetic or other medication in the body does not have to be accounted for by medication delivery controller 108 because the TCI system compensates for this. Thus, this reduces the overall order of the system to be controlled, giving a much faster result. Also, this provides an easy way of quickly checking the actions of medication delivery controller 108, as a particular blood or effect-site concentration of the drug can be easily related to a certain effect. Moreover, medication delivery controller 108 can be programmed to not go beyond certain limits, such as those on dosage or duration of drug administration, in order to avoid dangerous conditions.

In one embodiment, the invention utilizes RUGLOOP® as the pharmacokinetic (PK) TCI program. The RUGLOOP program was written by Tom De Smet and Michel Struys. Another embodiment uses STANPUMP as the PK TCI program; this program was written by Steven L. Shafer, M.D. of Stanford University, Anesthesiology Service (112A) PAVAC, 3801 Miranda Avenue, Palo Alto, Calif. 94304, and is freely available from the author. These TCI programs are capable of steering both blood and effect-site concentration. RUGLOOP is described in a thesis written by Tom De Smet and entitled "Ontwerp Van Een Computergestuurd closed-loop Anesthesiesysteem (Design of a Computer-Controlled Closed-Loop Anesthesia System)," filed at the Department of Electronics and Information Systems, Faculty of Applied Sciences, University of Gent, 1995. The algorithms in RUGLOOP are adapted from Shafer, S. L. and Gregg, K. M., "Algorithms to Rapidly Achieve and Maintain Stable Drug Effect with a Computer-Controlled Infusion Pump", J. Pharmacokinetics Biopharm. 20(2):147-169 and Shafer, S. L., Siegel, L. C., Cooke, J. E. and Scott, J. C. "Testing Computer-Controlled Infusion Pumps by Simulation", Anesthesiology, 68:261-266, 1988. RUGLOOP is freely available from Aspect Medical Systems, Newton, Mass.

Because RUGLOOP is used in one embodiment, preset pharmacokinetic parameters can be used without modification. A population-based Hill curve is used and the Bayesian method utilized to adapt it to an individual patient's specific response. One embodiment utilizes. RUGLOOP to steer a desired effect-site concentration, corresponding to a certain effect set point preprogrammed by the anesthetist or clinician during the start-up procedure. To reach and maintain the desired effect set point, the population-based Hill curve may be adapted to an individual patient using induction information. The Bayesian method described above may be used to adapt the Hill curve to changes occurring in the patient during surgical or other stimulation.

As stated above, other vital measures can be used in determining changes to be made in the administration of the medication. For example, in an anesthetic application, measures such as $SpO_2$, $ETCO_2$ and HR can be logged by the microprocessor to monitor safe administration of the medication. Alarms can be provided in order to warn the anesthetist or user of dangerous situations.

As stated above, medication delivery unit 112 can be implemented utilizing a variety of technologies. In one embodiment, a Graseby® 3400 syringe pump is implemented as medication delivery unit 112. This pump is capable of communicating with a controller via an RS-232 interface. Pump infusion rates can be set between 0 and 1200 ml/hour by medication delivery controller 108 in these embodiments. It is important to note that problems with adequate drug administration using syringe pumps can appear when the infusion rates change very frequently, especially in the low rate range. Particularly, with some pumps, the error between the calculated infusion volume and real volume administered increases with increasing rate-change frequency and decreasing average administration rate. Therefore, precautions are included in the algorithm to decrease the frequency of sending a new calculated pump rate to the syringe pump. For example, instead of sending a new calculated rate to the pump every three seconds, medication delivery controller 108 is set up to send a new calculated pump rate once every ten seconds, yielding a more accurate administration. In this specific example, the ten-second interval is chosen as it is the time range for a new calculation from the pharmacokinetic model algorithm.

In one embodiment, for reasons of safety, the option is provided to the anesthetist to return to open-loop control during administration of the medication. In this mode, the controller remains in a standby mode and the patient's response profile is available if it is desired to return to the closed-loop mode. In the open-loop mode, medication delivery controller 108 can be set to deliver the medication at a specific concentration as set by the user. In one embodiment, even when the administration of medication is canceled or put on hold by the operator, medication delivery controller 108 remains online and continues to update the patient's response profile and calculate the patient's concentration of medication even if no medication is delivered. Therefore, after the operator wishes to cease override, medication delivery controller can again enter the closed-loop mode and restart its action. As such, the medication delivery controller 108 uses the remaining concentration of medication at that moment and calculates how much medication is required to reach and maintain the set point concentration.

In one embodiment, medication delivery controller 108 queries the anesthetist Or operator whether he or she agrees with the lowest point calculated for the response profile. If this lowest value does not make sense the anesthetist or operator, using clinical judgment and experience, can change the value to a lower or higher level. Then, the response profile can be recomputed with the new lowest value.

As stated above, in one embodiment the closed loop controller uses the patient individualized pharmacodynamic relation to manage the function of the controller. During closed loop operation, medication delivery controller 108 uses the measured values to calculate a target concentration value for the delivery unit program that will realize the corresponding infusion regimen. A TCI system can be used to reduce the input-output complexity because it allows the blood or effect-site concentration to be targeted instead of the pump infusion rate. As a result, third-order pharmacokinetic behavior of the anesthetic in the body is bypassed. This results in reduced overall order of the system to be controlled and assures better results than using a PID (proportional-integral-derivative) controller to control the infusion rate.

Software Embodiments

Figure 9:
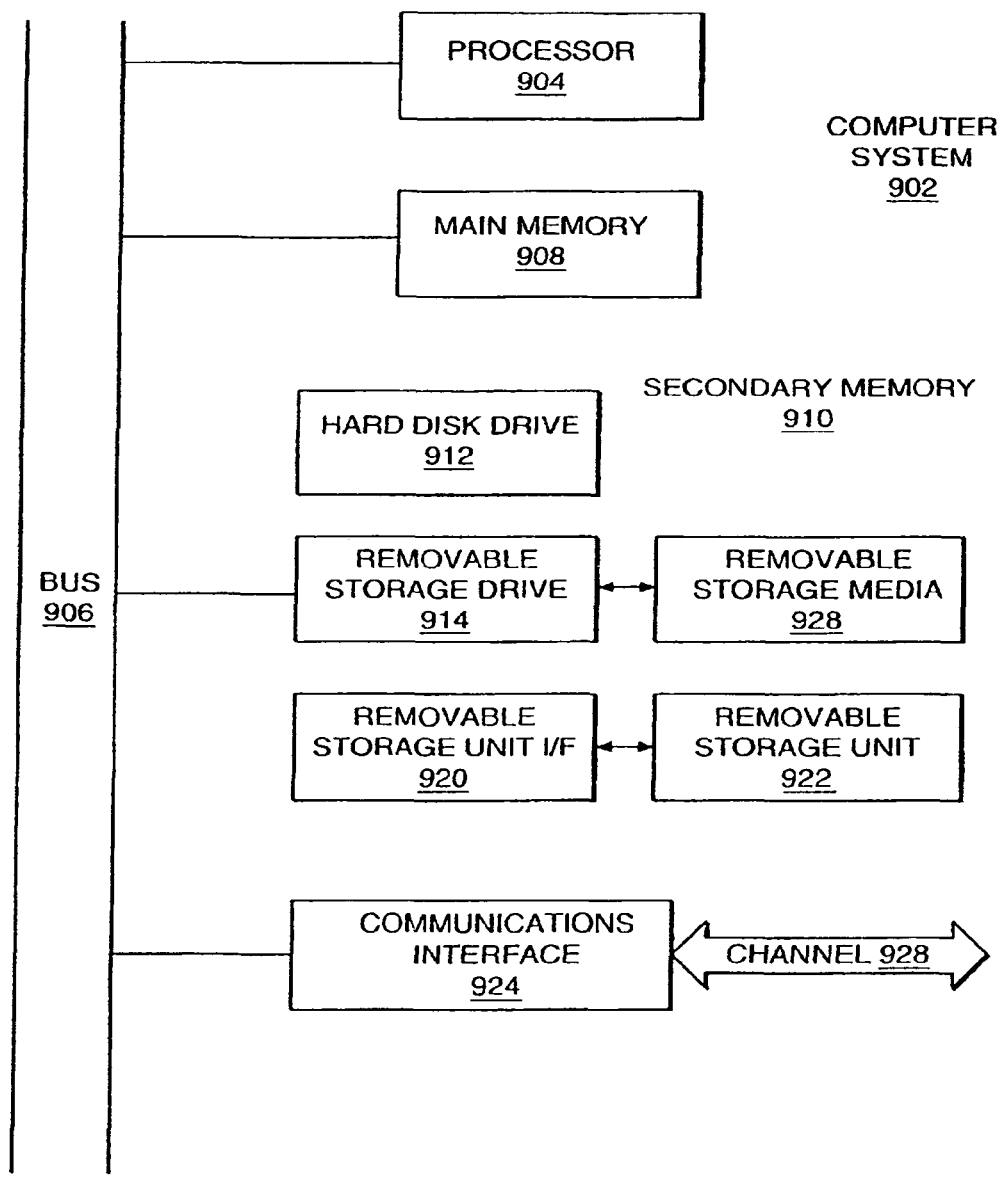
FIG. 9 is a block diagram illustrating an example architecture of a computer system which can be used to implement the functionality of the invention in accordance with one embodiment.

The various components of the invention can be implemented using hardware, software or a combination of both. FIG. 9 is a block diagram illustrating a general-purpose computer system, including examples of computer readable media for providing computer software or instructions to perform the functionality described herein. The illustrated computer system 902 includes one or more microprocessors, such as microprocessor 904. The microprocessor 904 is connected to a communication bus 906. Various software embodiments are described in terms of this example computer system. After reading this description, it will become apparent to a person of ordinary skill in the relevant art how to implement the invention using other computer systems or computer architectures, including, for example, the architectures or portions of the architectures illustrated in FIGS. 1, 6 and 8.

Computer system 902 also includes a main memory 908, preferably Random Access Memory (RAM), and can also include a secondary memory 910. The secondary memory 910 can include, for example, a hard disk drive 912 and/or a removable storage drive 914, representing a floppy disk drive, a magnetic tape drive, an optical disk drive, etc. Removable storage drive 914 reads from and/or writes to removable storage media 928. Removable storage media 928, represents a floppy disk, magnetic tape, optical disk, etc., which is read by and written to by removable storage drive 914. As will be appreciated, the removable storage media 928 includes a computer-usable storage medium having therein computer software and/or data.

In alternative embodiments, secondary memory 910 includes other similar means for allowing computer programs or other instructions to be loaded into computer system 902. Such means can include, for example, a removable storage unit 922 and a removable storage unit interface 920. Examples of such can include a program cartridge and cartridge interface (such as, for example, that found in video game devices), a removable memory chip (such as, for example, an EPROM, PROM or other memory device) and associated socket, and other removable storage units 922 and removable storage unit interfaces 920 which allow software and data to be transferred from the removable storage unit 922 to computer system 902. In some embodiments, removable storage unit 922 may be affixed permanently to removable storage unit interface 920.

Computer system 902 can also include a communications interface 924. Communications interface 924 allows software and data to be transferred between computer system 902 and external devices. Examples of communications interface 924 can include a modem, a network interface (such as an Ethernet card), a communications port, a PCM-CIA slot and card, etc. Software and data transferred via communications interface 924 are in the form of signals which can be electronic, electromagnetic, optical or other signals capable of being received by communications interface 924. These signals are provided to communications interface 924 via a channel 928. This channel 928 carries signals and can be implemented using a wireless medium, wire or cable, fiber optics, or other communications medium. Some examples of a channel can include a phone line, a cellular phone link, an RF link, a network, the Internet, and other communications channels.

In this document, the terms "computer program medium" and "computer usable medium" are used to generally refer to media such as removable storage media 928, a hard disk installed in hard disk drive 912, removable storage unit 922 and signals on channel 928. These terms can also refer to main memory 908 where main memory 908 stores a computer program or a part thereof. These computer program products are means for providing software to computer system 902.

Computer programs or instructions (also called computer control logic) can be stored in main memory 908 and/or secondary memory 910. Computer programs can also be received via communications interface 924. Such computer programs, when executed, enable the computer system 902 to perform the features of the present invention as discussed herein. In particular, the computer programs, when executed, enable the microprocessor 904 to perform the features of the present invitation. Accordingly, such computer programs represent controllers of the computer system 902.

In an embodiment where the elements are implemented using software, the software may be stored in a computer program product and loaded into computer system 902 using removable storage drive 914, removable storage unit 922, and hard drive 912 or communications interface 924. The control logic (software), when executed by the microprocessor 904, causes the microprocessor 904 to perform the functions of the invention as described herein.

In another embodiment, the elements are implemented primarily in hardware using, for example, hardware components such as Application Specific Integrated Circuits (ASICs). Implementation of the hardware state machine so as to perform the functions described herein will be apparent to persons of ordinary skill in the relevant art(s). Although not a "computer program" in the traditional sense, the hardware components can be thought of as a computer program medium (albeit, perhaps hard-wired) which enables the system to perform the described functions. In yet another embodiment, elements are implemented using a combination of both hardware and software. In this embodiment, the combination of the hardware and software can likewise be thought of as a computer program medium that enables the system to perform the described functions.

While various embodiments of the present invention have been described above, it should be understood that they have been presented by way of example only, and not limitation. Thus, the breadth and scope of the present invention should not be limited by any of the above-described exemplary embodiments, but should be defined only in accordance with the following claims and their equivalents.

What is claimed is:

1. A method of controlling delivery of medication with an electronic medication delivery controller, comprising the steps of:
    sampling, using at least one physiological sensor, data from a patient during the delivery of medication to the patient by a medication delivery unit;
    establishing, using said electronic medication delivery controller, a medication response profile;
    repeatedly updating, using said electronic medication delivery controller, in a closed loop process, the medication response profile using said data sampled from the patient by adapting parameters of said medication response profile, said medication response profile being indicative of a relationship between a concentration of the medication and an effect of the medication;
    minimizing, using said electronic medication delivery controller, the error between said updated medication response profile and the said sampled data; and
    adjusting, using said electronic medication delivery controller, the delivery of medication to the patient by the medication delivery unit based on the updated medication response profile.

2. The method of controlling the delivery of medication of claim 1, wherein an initial medication response profile is a population-derived medication response profile.

3. The method of controlling the delivery of medication of claim 1, wherein an initial medication response profile is a patient-specific medication response profile calculated from data sampled during an initial administration of the medication.

4. The method of controlling the delivery of medication of claim 2 wherein said parameters of said medication response profile are adapted to the patient in a controlled manner by a weighted combination of said sampled data and said initial medication response profile.

5. The method of controlling the delivery of medication of claim 3 wherein said parameters of said medication response profile are adapted to the patient in a controlled manner by a weighted combination of said sampled data and said initial medication response profile.

6. The method of controlling the delivery of medication of claim 1 wherein each parameter of the medication response profile is individually adapted.

7. The method of controlling the delivery of medication of claim 1 wherein the minimizing the error step further comprises using a minimization technique on a single merit function.

8. The method of controlling the delivery of medication of claim 7, wherein the extent to which the sampled data is used to update said medication response profile to changes in patient response is weighted based on an age of said data.

9. The method of controlling the delivery of medication of claim 8 wherein said age-weighted sample data is converted to an equivalent single-sample value to improve an objective weighing of all contributing factors in a merit function, irrespective of the number of samples.

10. The method of controlling the delivery of medication of claim 7 further comprising the step of calculating, using said electronic medication delivery controller, an estimate of a goodness-of-fit of the obtained medication response profile.

11. The method of controlling the delivery of medication of claim 10 further comprising the step of determining, using said electronic medication delivery controller, whether to use the calculated medication profile in the closed-loop operation based on said estimate of said goodness-of-fit.

12. The method of controlling the delivery of medication of claim 10 further comprising the step of setting, using said electronic medication delivery controller, a new medication response profile as an initial medication response profile during medication administration based on the calculated goodness-of-fit.

13. The method of controlling the delivery of medication of claim 1 further comprising the steps of:
    continuing to sample data using said at least one physiological sensor; and
    updating, using said electronic medication delivery controller, the medication response profile if the process operates in a temporary open-loop state.

14. The method of controlling the delivery of medication of claim 1, wherein the medication response profile is established prior to operating in the closed loop process.

15. A medication delivery system comprising:
    at least one physiological sensor for sampling data from a patient during delivery of medication to the patient by a medication delivery unit; and
    a medication delivery controller comprising a processor that is configured to:
        establish a medication response profile;
        update said medication response profile using said data sampled from the patient by adapting parameters of said medication response profile, said medication response profile indicative of a relationship between a concentration of the medication and an effect of the medication;
        minimize an error between said sampled data and said updated medication response profile; and
        adjust the delivery of medication to the patient by the medication delivery unit based on the updated medication response profile.

* * * * *